United States Patent [19]

Swanson et al.

[11] Patent Number: 5,942,555
[45] Date of Patent: Aug. 24, 1999

[54] PHOTOACTIVATABLE CHAIN TRANSFER AGENTS AND SEMI-TELECHELIC PHOTOACTIVATABLE POLYMERS PREPARED THEREFROM

[75] Inventors: Melvin J. Swanson, Carver; Richard A. Amos, St. Anthony; Dale G. Swan; Gary W. Opperman, both of St. Louis Park, all of Minn.

[73] Assignee: SurModics, Inc., Eden Prairie, Minn.

[21] Appl. No.: 08/619,303

[22] Filed: Mar. 21, 1996

[51] Int. Cl.$^6$ .................... C08L 101/02; C08G 75/04; C08G 75/10; C08J 7/18

[52] U.S. Cl. .................. 522/35; 522/13; 522/40; 522/41; 522/42; 522/43; 522/44; 522/46; 522/49; 522/48; 522/904; 522/905; 528/220; 528/224; 528/222; 528/306; 528/374; 528/376; 568/63; 568/20; 526/224; 526/313

[58] Field of Search ................ 522/35, 13, 40, 522/41, 42, 43, 44, 49, 46, 27, 12–23, 48, 904, 905; 568/63, 20; 528/220, 224, 222, 306, 374, 376

[56] References Cited

U.S. PATENT DOCUMENTS

| | | | |
|---|---|---|---|
| 3,969,327 | 7/1976 | Stein et al. | 526/1 |
| 4,177,338 | 12/1979 | Vrancken et al. | 526/111 |
| 4,312,726 | 1/1982 | Vrancken et al. | 526/211 |
| 5,002,582 | 3/1991 | Guire et al. | |
| 5,073,611 | 12/1991 | Rehmer et al. | 522/905 |
| 5,190,989 | 3/1993 | Himori | 522/57 |
| 5,248,805 | 9/1993 | Boettcher et al. | 558/270 |
| 5,376,503 | 12/1994 | Audett et al. | 522/905 |
| 5,399,642 | 3/1995 | Emmons et al. | |
| 5,412,051 | 5/1995 | McCallum, III et al. | |
| 5,532,112 | 7/1996 | Kohler et al. | 430/281 |

OTHER PUBLICATIONS

T. Otsu et al., "Living Radical Polymerization in Homogeneous System by Using Iniferter: Design of Block Copolymers", J. Macromol. Sci.–Chem., A21(889), pp. 961–977, Nov. 1984.

Veronese et al., "Hydroxyl–Terminated Polyvinylpyrrolidone for the Modification of Polypeptides", J. Bioactive and Compatible Polymers, 5:167–178 (1990).

Takei et al. "Temperature Responsive Bioconjugates", Bioconjugate Chem. 4:42–46 (1993).

"Radical Polymerization", pp. 941–956, in Concise Encyclopedia of Polymer Science and Engineering, Kroschwitz, ed., John Wiley and Sons, 1990.

"Developments in Polymerization", Chapt. 1, pp. 1–21, in New Methods of Polymer Synthesis, J. Ebdon, ed., Chapman and Hall, 1991.

"Plastics", pp. 462–464, in Concise Encyclopedia of Polymer Science and Engineering, Kroschwitz, ed., John Wiley and Sons, 1990.

"Telomerization", pp. 1163–1164 in Concise Encyclopedia of Polymer Science and Engineering, Kroschwitz, ed., John Wiley and Sons, 1990.

Takei, Y.G., et al. Bioconi, Chem. 4:42 (1993).

Andreani, F., et al., J. Bioactive and Compatible Polymers, 1:72 (1986).

"Terminally reactive oligomers: telechelic oligomers and macromers", pp. 162–196, J. Ebdon, Chapt. 6, in New Methods of Polymer Synthesis, Chapman and Hall, 1991.

S. Kamei, et al., Pharm. Res. 12(5):663–668 (1995).

Andreani et al. "Synthesis of Functionalized End–capped N–vinylpyrrolidone Telomers with Potential Utility as Drug––Binding Matricies", J. Bioactive and Compatible Polymers 1:72–78 (1986).

Primary Examiner—Susan W. Berman
Attorney, Agent, or Firm—Fredrikson & Byron, P.A.

[57] ABSTRACT

A photoactivatable reagent useful as a chain transfer reagent for providing a semitelechelic polymer having one or more terminal photoactivatable groups. The reagent provides one or more photoactivatable groups and one or more sulfhydryl (or other chain transfer) groups, the photoactivatable and chain transfer groups optionally being joined together by a spacer group. The reagent can be used to prepare a polymer by serving to initiate the polymerization of ethylenically unsaturated monomers. The reagent itself becomes an integral part of the resultant polymer, thereby providing the polymer with a terminal photoactivatable nature. The method provides a number of benefits, including the ability to provide homogeneous photoactivatable polymer compositions, e.g., in terms of the uniform location of the photogroup(s) on the terminal portion of each polymer molecule and the ability to build a desired nonpolar quality, and in turn improved surfactancy, into otherwise polar polymers.

27 Claims, No Drawings

PHOTOACTIVATABLE CHAIN TRANSFER AGENTS AND SEMI-TELECHELIC PHOTOACTIVATABLE POLYMERS PREPARED THEREFROM

TECHNICAL FIELD

The present invention relates to the field of reagents such as chain transfer agents useful for controlling the molecular weight of synthetic polymers. In another aspect, the invention relates to polymers having photoactivatable (i.e., photoreactive) groups incorporated therein, and to methods for preparing such polymers. In yet a further aspect, the invention relates to photoactivatable polymers useful for modifying surfaces by the attachment of the polymers to the surface, via activated photo groups.

BACKGROUND ART

It is often desirable to modify the surface of a material for such purposes as making an otherwise nonwettable surface wettable, passivating the surface, making the surface more amenable to adhesive bonding, or immobilizing desired molecules onto the surface. For example, hydrophobic membranes made from polysulfone, polycarbonate or polyvinylidene difluoride can be made permanently wettable by the attachment of hydrophilic polymers. Similarly, such membranes can be "passivated" by attaching polymers that serve to prevent the adsorption of proteins or lipids that could foul the membranes.

Membranes or other porous materials can also be modified in order to immobilize binding proteins, such as antibodies or other receptors, for use as affinity purification media. Likewise, materials that are difficult to bond, such as polyolefins or silicone rubber, can be modified with a primer to allow stronger bonds to other materials. Methods have also been described for modifying surfaces by the immobilization of photopolymers. U.S. Pat. No. 5,002,582, for instance, describes such methods and is incorporated herein by reference.

On a separate subject, the term "telomerization" was originally used to describe the free radical polymerization of ethylene. Today, this word can be defined more broadly as the process of reacting, under polymerization conditions, a telogen (AB) with more than one unit of a taxogen (e.g., a polymerizable compound having ethylenic unsaturation) in order to form products called telomers. A telomer has the formula $A(C)_nB$ where $(C)_n$ (with "C" being called a taxomon) is a divalent radical formed by chemical union of molecules of the taxogen, n is greater than one, and A and B are fragments of the original telogen, now attached to the terminal taxomons. Telomerization can now be used to describe polymerization methods that include free radical, anionic, cationic, and transition metal catalyzed processes. See, for instance, "Telomerization", pp. 1163–1164 in *Concise Encyclopedia of Polymer Science and Engineering*, Kroschwitz, ed., John Wiley and Sons, 1990, the disclosure of which is incorporated herein by reference.

Polymerization processes have previously been described that include the use of compounds, known as "chain transfer agents", to control the weight of synthetic polymers. Methods for the synthesis of polymers having certain functional groups at one end have been previously reported. Takei, Y. G., et. al. *Bioconj. Chem.* 4:42 (1993) and Andreani, F.et.al., *J. Bioactive and Compatible Polymers*, 1:72 (1986) describe such methods and are incorporated herein by reference. Such polymers have been described as "telechelic", meaning a polymer having a functional endgroup such as a terminal hydroxyl, thiol, halide, carboxyl or amine group. See, e.g., "Terminally reactive oligomers: telechelic oligomers and macromers", pp. 162–196, J. Ebdon, Chapt. 6, in *New Methods of Polymer Synthesis*, Chapman and Hall, 1991. Alternatively, the word "semitelechelic" can be used to refer to a linear macromolecule possessing a functional group at one end of the molecule. (See, e.g., S. Kamei, et al., *Pharm. Res.* 12(5):663–338 (1995).

U.S. Pat. No. 5,399,642 describes latent thiol mercaptan chain transfer agents, and their use in the synthesis of polymers. The polymers have at least one protected thiol group, said to be primarily at the terminal portion of the chain. The polymer can be used with the thiol group in its protected form, or the thiol group can be deprotected to yield a terminal thiol group capable of reacting with other monomers to form a block copolymer.

U.S. Pat. No. 5,412,015 describes polymers having at least one amine sulfide terminal moiety, imparted by the use of amine-thiols as chain transfer agents. See also, Andreani et al. "Synthesis of Functionalized End-capped N-vinylpyrrolidone Telomers with Potential Utility as Drug-Binding Matricies", *J. Bioactive and Compatible Polymers* 1:72–78 (1986); Veronese et al., "Hydroxyl-Terminated Polyvinylpyrrolidone for the Modification of Polypeptides", *J. Bioactive and Compatible Polymers*, 5:167–178 (1990); and Takei et al. "Temperature Responsive Bioconjugates", *Bioconjugate Chem.* 4:42–46 (1993).

Applicants are unaware, however, of any art that teaches or suggests either the preparation or use of chain transfer agents to provide polymers having terminal photoactivatable groups.

SUMMARY OF THE INVENTION

The present invention provides a photoactivatable reagent useful as a chain transfer reagent for providing a semitelechelic polymer having one or more terminal photoactivatable groups. The word "semitelechelic", when used with respect to a polymer of this invention, will refer to a polymer in which one or more photoactivatable groups are provided by the group forming one end of the polymer. Generally, and preferably, that end group is the residue of a chain transfer agent that was used to initiate the polymer, and that itself provided the photoactivatable group(s).

In another aspect, the reagent comprises one or more photoactivatable groups and one or more chain transfer groups, the chain transfer groups serving to terminate the free radical polymerization of a polymer chain by donating an atom to a propagating free radical, and in turn, the reagent serving as an initiation site for the growth of a new polymer chain in order to provide a semitelechelic polymer having an end group comprising one or more photoactivatable groups.

A chain transfer agent of this invention comprises one or more photoactivatable groups and a sulfhydryl (or other chain transfer group), the photoactivatable and chain transfer groups optionally being joined together by a spacer group.

Preferably the reagent is provided in the form of a photoactivatable mercaptan chain transfer agent having the general formula:

$$Y_i\text{—}X\text{—}SH$$

where Y is an organic radical comprising one or more photoactivatable groups, X is optional, and if present is a di- or higher order organic radical that serves as a spacer, i is $\geq 1$, and SH is a sulfhydryl radical.

In another aspect, the invention provides a method of preparing a polymer, the method comprising the step of initiating the polymerization of monomers, e.g., ethylenically unsaturated monomers, by the use of a reagent of the present invention. The reagent becomes an integral part of the resultant polymer, thereby providing the polymer with its photoactivatable nature. The chain transfer reagent can also serve to terminate chain growth, e.g., by hydrogen atom transfer, thus providing a reinitiation site for the growth of a new polymer chain.

In yet another aspect, the invention provides a synthetic polymer prepared using a chain transfer reagent of the present invention, the polymer comprising polymerized monomer units, e.g., polymerized ethylenically unsaturated monomers, and at least one terminal photoactivatable group.

In yet a further aspect, the invention provides surfaces modified using synthetic polymers as described above, as well as a method of modifying such surfaces.

Reagents of the present invention provide a number of benefits, including the ability to provide homogeneous photoactivatable polymer compositions, e.g., in terms of the uniform location of the photogroup(s) on the terminal portion of each polymer molecule. By virtue of the present invention, a reagent composition can be readily prepared and used, the composition comprising homogeneous populations of individual polymer molecules, each having one or more terminal photogroup(s).

In addition to providing improved selection and control of the location of photoactivatable groups in a polymer, the reagent of the present invention also permits improved control of the molecular weight, and reduced molecular weight dispersity, of the resulting photopolymers. Those skilled in the relevant art, given the present description, will be able to determine a proper molar ratio for the polymerizable monomers and chain transfer agent of the present invention. In turn, they will be able to control the average molecular weight and number of terminal photogroups in the resulting population of photopolymer molecules.

Reagents of the invention also provide benefits in terms of the ability to build a desired nonpolar quality into otherwise polar polymers, resulting in improved surfactancy. Preferred photoactivatable groups, such as benzophenone, can be used to provide a hydrophobic quality, i.e, at the terminal portion, to an otherwise hydrophilic polymer. Such a quality can permit the polymer to be used, e.g., applied to a surface, in a manner not generally feasible between a hydrophilic polymer and hydrophobic surface.

In turn, preferred polymers of the present invention can be applied to a surface in a straightforward method that comprises the steps of contacting the surface with the polymer under conditions in which the hydrophobic portions are able to orient themselves to the hydrophobic surface. Thereafter, the photogroups can be activated in order to covalently attach the polymer molecules in their oriented position. As a result, such polymers can be used without the need to first derivatize the polymer or treat the surface in order to render it wettable with aqueous solutions.

In summary, the present invention provides several advantages over the current art for the preparation of photopolymers. Those advantages include the ability to provide endpoint incorporation of the photoactivatable group, improved control of molecular weight and reduced molecular weight dispersity. The advantages also include the ability to prepare a polymer having improved surfactant action to control orientation of the molecule on the surface to be coated.

DETAILED DESCRIPTION

The present invention provides, inter alia, a reagent useful as a chain transfer agent, for preparing photoactivatable polymers having one or more terminal latent reactive (i.e., photoreactive) groups. By "terminal" is meant that the reagent providing one or more photoactivatable groups is incorporated into and present at an end of the polymer chain.

The word "photoactivatable", and inflections thereof, will be used interchangeably with the word "photoreactive" and its inflections, in order to refer to a chemical group that responds to an applied external energy source in order to undergo active specie generation, resulting in covalent bonding to an adjacent chemical structure (e.g., a carbon having an abstractable hydrogen).

Photopolymers of the present invention can be prepared using a free-radical polymerization comprising four elementary steps: initiation, propagation, termination, and chain transfer employing a photoactivatable chain transfer agent. See, e.g., "Radical Polymerization", pp.941–956, in *Concise Encyclopedia of Polymer Science and Engineering*, Kroschwitz, ed., John Wiley and Sons, 1990, the disclosure of which is incorporated herein by reference.

The chain transfer agent of the present invention can be used in a reaction scheme as outlined in Takei, Y. G., et. al. (cited and incorporated above). The initiator for the polymerization reaction begins the reaction process by the generation of free radicals. The free radicals are each capable of undergoing an atom transfer reaction with a respective chain transfer reagent of this invention in order to leave the radical center on the latter species. As a radical, the chain transfer reagent then adds to a monomer to form an active center.

The propagation, or growth reaction, then consists of the rapid addition of monomer molecules to the radical species, usually in a head-to-tail fashion. In termination, growth of polymer chains is brought to an end by the destruction of propagating radicals via dimerization of two radicals. Alternatively, a free radical can be used to abstract an atom (e.g., hydrogen) from a saturated molecule (the chain transfer agent) in order to cease the growth of the propagating radical, and at the same time produce a new, small radical which may itself reinitiate a new polymer chain. In so doing, the chain transfer agent itself becomes a new initiation site and forms the end group of the resultant polymer.

The term "chain transfer", as used herein, therefore refers to an atom abstraction process that may involve any species present in a free radical polymerization process. "Chain transfer agent" refers to a reagent, e.g. monomer, initiator, solvent, polymer, or some other species that has been added deliberately to effect chain transfer. Finally, "chain transfer group" will refer to that portion (or portions) of a chain transfer agent that provides the desired chain transfer function. A chain transfer reagent of the invention can serve other purposes as well, e.g., the word "iniferter" can be used to describe a reagent which upon decomposition generates a pair of free radicals, thus serving as both an initiator and a chain transfer reagent.

A reagent of the present invention provides a photoactivatable chain transfer agent, the reagent being useful for terminating a polymerization reaction in order to form a new species capable of reinitiating new chain growth to incorporate the photoreagent into the resulting polymer.

Preferably, such polymers are synthesized by free radical polymerization using reagents of the present invention, the reagents having both photoactivatable groups and chain transfer groups such as sulfhydryl groups that function as free radical chain transfer agents.

The polymers prepared by use of such reagents typically have greater surfactant character and orient more favorably (i.e., with photogroups toward the hydrophobic surface and hydrophilic polymer away from the surface) than do photopolymers having randomly distributed photogroups.

In another aspect, the invention provides a method of preparing photoactivatable polymers having one or more photogroups provided by an end group, the method comprising the steps of:

(a) providing a reagent comprising a photoactivatable chain transfer agent having one or more photoactivatable groups, and (b) providing a composition comprising one or more polymerizable monomers and one or more free radical initiators, and (c) initiating a polymerization reaction and employing the photoactivatable chain transfer agent in the composition under conditions suitable to allow the agent to initiate the polymerization of monomers, thereby incorporating the reagent, and in turn the photoactivatable group(s), into the polymer.

PREPARATION OF PHOTOACTIVATABLE CHAIN TRANSFER AGENTS

Preferred reagents of the present invention provide one or more photoactivatable groups and one or more chain transfer (e.g., sulfhydryl) groups joined together, optionally, by means of a spacer radical. In a particularly preferred embodiment, the chain transfer agent comprises two photoactivatable groups and one sulfhydryl group.

A chain transfer agent of this invention comprises one or more photoactivatable groups, a spacer region, and a sulfhydryl group. A preferred agent of the invention can be described by the following general structure:

$$Y_i\text{—}X\text{—}SH$$

where Y is an organic radical comprising, independently, one or more photoactivatable groups, X is optional, and if present is a di- or higher order organic radical that serves as a spacer, i is $\geq 1$, and SH is a sulfhydryl radical.

Terminal "Y" Groups

In a preferred embodiment one or more photoactivatable groups are provided by the Y group attached to the X radical. Preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum being particularly preferred.

Photoactivatable aryl ketones are preferred, such as acetophenone, benzophenone, anthraquinone, anthrone, and anthrone-like heterocycles (i.e., heterocyclic analogues of anthrone such as those having N, O, or S in the 10- position), or their substituted (e.g., ring substituted) derivatives. The functional groups of such ketones are preferred since they are readily capable of undergoing the activation/inactivation/reactivation cycle described herein.

Benzophenone is a particularly preferred photoactivatable group, since it is capable of photochemical excitation with the initial formation of an excited singlet state that undergoes intersystem crossing to the triplet state. The excited triplet state can insert into carbonhydrogen bonds by abstraction of a hydrogen atom (for example, from a support surface or target molecule in the solution and in bonding proximity to the agent), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Hence, photoactivatable aryl ketones are particularly preferred.

Optionally, the photogroups can themselves be derivatized, e.g., in order to improve or alter the hydrophobicity or other physico-chemical characteristics of the group as a whole. The derivatized Y group, in turn, can be used to provide the altered or improved characteristics to the chain transfer agent, and in turn, to a polymer formed therefrom. Examples of the preparation and use of derivatized photogroups are provided herein, e.g., Compound VIII at Example 10.

Spacer "X" Groups

Spacer regions of the present invention, identified as "X" groups, can include any di- or higher-valent organic radical. Suitable spacer radicals provide an optimal combination of such properties as hydrophobicity/hydrophilicity, reactivity suitable for the incorporation of Y and SH groups, a substitution pattern to permit easy incorporation of multiple groups, good chemical stability of the linking functional groups, and good photochemical stability to prevent degradation during the photoimmobilization process.

Examples of suitable spacer radicals include, but are not limited to the group consisting of substituted or unsubstituted alkylene, oxyalkylene, cycloalkylene, arylene, oxyarylene, or aralkylene group and having amides, ethers, esters, and carbamates as linking functional groups to the photoactivatable group and chain transfer agent.

Examples of preferred spacer radicals include, but are not limited to;

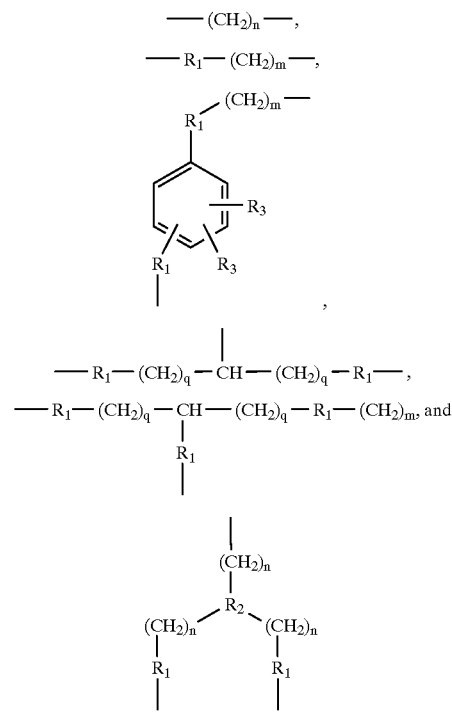

Wherein:

-continued

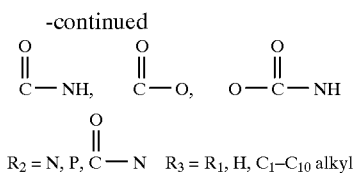

and wherein q=0–16, n=1–16, and m=2–16.

Chain Transfer Groups

Suitable chain transfer groups for use in a reagent of the present invention provide an optimal combination of such properties as the ability to function as chain terminators along with the ability to efficiently reinitiate polymerization by effectively carrying the radical center to the remaining monomer present. An efficient chain transfer agent will be able to control the average molecular weight without significant reduction in the overall rate of polymerization. In addition, good chemical stability of the group is needed to enhance storage life for the reagent.

Examples of suitable chain transfer groups include, but are not limited to, sulfhlydryl compounds, arylacetonitriles, 2-aryl acetates and derivatives of indene, fluorene, α-phenylpropiolactone, and pentaphenylethane. An example of a particularly preferred chain transfer group is the sulfhydryl group.

Preparation of Reagents and Polymers

Those skilled in the art, guided by the present description and Examples, will have available a variety of suitable methods for the synthesis of photoactivatable chain transfer agents within the scope of this invention. Preferable is the selection of spacer groups having a minimum of two functional groups with distinctly different chemical reactivities to permit differential incorporation of the photoactivatable group(s) and the chain transfer group using organic chemistry coupling techniques well known to those skilled in the art. For example, the —SH chain transfer group can be incorporated using a heterobifunctional molecule containing both the —SH and an amine group, using the latter group to couple to an acid chloride or activated ester on the spacer group to form a stable amide linkage. Alternatively, the —SH group can be formed by a ring opening reaction of a gamma-thiobutyrolactone using an amine functionality on the spacer group.

The photoactivatable group can be introduced by an alkylation reaction using a photoactivatable benzyl halide with hydroxyl groups on the spacer to provide coupling through the Williamson ether synthesis. Alternatively, the photoactivatable group can be delivered as an acid chloride for reaction with amines on the spacer group to provide stable amide linking groups. These nonlimiting examples demonstrate the versatility of synthetic methods available for the incorporation of the spacer group into the chain transfer reagent.

Photoactivatable chain transfer agents of the invention can be used in a variety of polymerization (including copolymerization) reactions that employ chain transfer agents, and in particular for free-radical polymerization reactions employing unsaturated monomers.

Suitable monomers are selected from the group consisting of monosubstituted or unsymmetrically (1,1-) disubstituted ethylenes, $CH_2=CHR_4$, and $CH_2=CHR_4R_5$. Preferred monomers for use in preparing a photopolymer of the present invention are selected from the group consisting of alpha-olefins, vinyl monomers and acrylic monomers.

The polymerization involves repeated free-radical addition to monomer double bonds, forming chains of carbon atoms constructed of units $—(CH_2=CHR_4R_5)—$ or $—(CH2—CR_4R_5)—$ linked in predominantly head-to-tail fashion (the substituted carbon atom being designated the head). The substituents $R_4$ and $R_5$ form side chains attached to the primary chains of the polymer. For purposes of the present invention, any side chains can be employed, e.g., alkyl groups, so long as they do not detrimentally affect the preparation or use of the polymer for its intended purpose. The appropriate selection of the side chains can also add to the versatility of the polymers by introducing reactive functionality on the polymer. For example, the use of monomers containing N-oxysuccinimidyl esters can be used to prepare photopolymers capable of reacting with the amine groups of other molecules. Alternatively, monomers containing vicinal diols can be used to prepare photopolymers which can be oxidized to generate aldehyde groups as a reactive functionality.

Examples of preferred monomers include, but are not limited to, acrylate esters and acids, methacrylate esters and acids, styrene and substituted styrenes, and allyl ethers and amines. Examples of particularly preferred monomers include acrylonitrile, methacrylonitrile, acrolein, acrylamide, N-vinylpyrrolidone, vinylphosphonic acid and esters, N-(3-aminopropyl) methacrylamide, 2-acrylamido-2-methylpropanesulfonic acid, allyl glycidyl ether, 3-allyloxy-1,2-propanediol, 2-vinyl-4, 4-dimethyl-2-oxazolin-5-one, and N-succinimidyl 6-maleimidohexanoate.

As described in "Developments in Polymerization", Chapt. 1, pp. 1–21, in *New Methods of Polymer Synthesis*, J. Ebdon, ed., Chapman and Hall, 1991, the chain transfer agent functions in a dual role: terminating a growing polymer chain by transfer of an atom from the chain transfer agent to the growing chain, followed by a reinitiation of the polymerization process begun by the radical center now residing on the chain transfer agent. The average molecular weight of the photopolymer formed will thus be controlled by the frequency with which the radical at the end of the growing chain encounters a new monomer molecule versus a chain transfer agent.

The ease of radical transfer will vary from system to system depending upon the nature of the monomer and the chain transfer agent because of differences in transfer constants. However, for a given combination of monomer and chain transfer agent, the molecular weight will be largely determined by the ratio of monomer/chain transfer agent. This ratio will control the statistical frequency with which these groups encounter one another. The chain transfer agents of this invention are preferably used in monomer/chain transfer agent molar ratios of 5:1 to 800:1, more preferably 10:1 to 300:1, and most preferably 20:1 to 150:1.

Free-radical polymerization is normally effected in the liquid phase, in bulk monomer, or in solution. For commercial large scale preparations, solution, suspension or emulsion polymerizations have several advantages.

Preferred photoactivatable chain transfer agents of the present invention include, but are not limited to, those shown in TABLE I below.

TABLE I

| Structure | Compound | Example |
|---|---|---|
| Ph-CO-C6H4-CH2SH | I | 3 |
| Ph-CO-C6H4-C(O)NH-(CH2)2-SH | II | 4 |
| 3,5-bis(4-benzoylbenzyloxy)-N-(2-mercaptoethyl)benzamide | III | 5 |
| Bis(4-benzoylbenzamido)-lysine-N-(2-mercaptoethyl)amide | IV | 6 |

TABLE I-continued

| Structure | Compound | Example |
|---|---|---|
| (structure) | V | 7 |
| (structure) | VI | 8 |
| (structure) | VII | 9 |
| (structure) | VIII | 10 |

Use of Photopolymers

Photoactivatable polymers of the present invention can be used in any suitable manner, including by the simultaneous or sequential attachment of the polymer to a support surface. Polymers of the present invention can be used to modify any suitable surface. Where the latent reactive group of the agent is a photoactivatable group of the preferred type, it is particularly preferred that the surface provide abstractable hydrogen atoms suitable for covalent bonding with the activated group.

Preferred photopolymers are water soluble in that they are soluble at a concentration of about 0.1 mg/ml, preferably at about 1 mg/ml and most preferably at about 10 mg/ml in aqueous systems. When dissolved in water, preferred polymers are able to reduce the surface tension of the aqueous solution, in a manner analogous to that of a detergent. The surfactant character of the polymer contributes, in turn, to the ability of such aqueous solutions to wet relatively hydrophobic polymeric surfaces. The hydrophobic character of the photogroups causes them to associate with hydrophobic surfaces, resulting in the polymers orienting with the photogroup end toward the surface and the hydrophilic end away from the surface, thus rendering the surface hydrophilic.

Plastics such as polyolefins, polystyrenes, poly(methyl) methacrylates, polyacrylonitriles, poly(vinylacetates), poly (vinyl alcohols), chlorine-containing polymers such as poly (vinyl) chloride, polyoxymethylenes, polycarbonates, polyamides, polyimides, polyurethanes, phenolics, amino-epoxy resins, polyesters, silicones, cellulose, and rubber can all be used as supports, providing surfaces that can be modified as described herein. See generally, "Plastics", pp. 462–464, in *Concise Encyclopedia of Polymer Science and Engineering*, Kroschwitz, ed., John Wiley and Sons, 1990, the disclosure of which is incorporated herein by reference. In addition, supports such as those formed of pyrolytic carbon and silylated surfaces of glass, ceramic, or metal are suitable for surface modification.

In one aspect, the present invention provides photoactivatable polymers having one or more photoactivatable groups at one end of the polymer, such polymers having been synthesized by free radical polymerization using compounds that contain photoactivatable groups and functional groups such as sulfhydryl groups that function as free radical chain transfer agents. The polymers synthesized by use of such compounds typically have greater surfactant character and orient more favorably (i.e., with photogroups toward the surface and hydrophilic polymer away from the surface) than do photopolymers having randomly distributed photogroups.

Any suitable technique can be used for attaching a photoactivatable polymer to a surface, and such techniques can be selected and optimized for each material, process, or device. The polymer can be successfully applied to clean material surfaces as listed above by spray, dip, or brush coating of a solution of the reactive linking agent. In a typical simultaneous application, the support intended for coating is first dipped in an aqueous solution of polymer. The coated surface is then exposed to ultraviolet or visible light in order to promote covalent bond formation between the linking agent, target molecule, and material surface, after which the support is washed to remove unbound molecules.

In a typical sequential application, the support is first coated with a solution of the polymer. By virtue of the hydrophobic nature of the photoactivatable group(s), the polymer molecules can be used to coat a hydrophobic surface under conditions suitable to allow the photogroups to orient themselves to the surface. Once oriented, the polymer-coated support is then exposed to ultraviolet or visible light in order to covalently bond the polymer to the support surface.

Polymers of the present invention can be used to modify surfaces in order to provide a variety of different or improved properties, e.g., to render an otherwise nonwettable surface wettable, to passivate the surface in order to prevent protein fouling, to make the surface more amenable to adhesive bonding, and to immobilize desired molecules onto the surface.

When desired, other approaches can be used for surface modification using the reagent and polymers of the present invention. Such approaches are particularly useful in those situations in which the support surface and polymer (including photogroups) do not demonstrate the desired extent of hydrophobic or hydrophilic attraction.

The invention will be further described with reference to the following nonlimiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Example 1

Preparation of 4-Benzoylbenzoyl Chloride

4-Benzoylbenzoic acid (BBA), 1.0 kg (4.42 moles), was added to a dry 5 liter Morton flask equipped with reflux condenser and overhead stirrer, followed by the addition of 645 ml (8.84 moles) of thionyl chloride and 725 ml of toluene. Dimethylformamide, 3.5 ml, was then added and the mixture was heated at reflux for 4 hours. After cooling, the solvents were removed under reduced pressure and the residual thionyl chloride was removed by three evaporations using 3×500 ml of toluene. The product was recrystallized from 1:4 toluene: hexane to give 988 g (91% yield) after drying in a vacuum oven. Product melting point was 92–94° C. Nuclear magnetic resonance (NMR) analysis at 80 MHz ($^1$H NMR (CDCl$_3$)) was consistent with the desired product: aromatic protons 7.20–8.25 (m, 9H). All chemical shift values are in ppm downfield from a tetramethylsilane internal standard. The final compound was stored for use in the preparation of photoactivatable chain transfer reagents, as described for instance in Examples 4 and 6.

Example 2

Preparation of 4-Bromomethylbenzophenone

4-Methylbenzophenone, 750 g (3.82 moles), was added to a 5 liter Morton flask equipped with an overhead stirrer and dissolved in 2850 ml of benzene. The solution was then heated to reflux, followed by the dropwise addition of 610 g (3.82 moles) of bromine in 330 ml of benzene. The addition rate was approximately 1.5 ml/min and the flask was illuminated with a 90 watt (90 joule/sec) halogen spotlight to initiate the reaction. A timer was used with the lamp to provide a 10% duty cycle (on 5 seconds, off 40 seconds), followed in one hour by a 20% duty cycle (on 10 seconds, off 40 seconds). At the end of the addition, the product was analyzed by gas chromatography and was found to contain 71% of the desired 4-bromomethylbenzophenone, 8% of the dibromo product, and 20% unreacted 4-methylbenzophenone. After cooling, the reaction mixture was washed with 10 g of sodium bisulfite in 100 ml of water, followed by washing with 3×200 ml of water. The product was dried over sodium sulfate and recrystallized twice from 1:3 toluene:hexane. After drying under vacuum, 635 g of 4-bromomethylbenzophenone were isolated, providing a yield of 60% and having a melting point of 112–114° C. Analysis on an NMR spectrometer was consistent with the desired product: $^1$H NMR (CDCl$_3$) aromatic protons 7.20–7.80 (m, 9H) and benzylic protons 4.48 (s, 2H). The final compound was stored for use in the preparation of photoactivatable chain transfer reagents, as described for instance in Examples 3, 5, and 7–9.

Example 3

Preparation of 4-Mercaptomethylbenzophenone (Compound I)

A photoactivatable chain transfer reagent of the present invention was prepared in the following manner, and used in the manner described in Example 13. Thiourea, 4.14 g (54.4 mmol), was dissolved in 31.5 ml of 95% ethanol, followed by the addition of 15.0 g (54.4 mmol) of 4-bromomethylbenzophenone, prepared according to the general method described in Example 2, in three portions using gentle warming to help dissolve the solids. The mixture was stirred overnight at room temperature. The solid product was isolated by filtration, rinsing the solid with ethanol. The solids were dried in a vacuum oven to give 15.64 g of product, an 82% yield. The product was used in the second step without further purification.

The isothiourea hydrobromide salt, 12.5 g (35.5 mmol), was dissolved in 250 ml of water with warming. A solution of 5.7 g of sodium hydroxide (0.143 mol) in 10 ml of water was then added to the salt solution and the mixture was refluxed 45 minutes. After cooling, the solution was acidified with concentrated sulfuric acid and the product was extracted with 5×60 ml of chloroform. The combined extracts were washed with 100 ml of water and then dried over sodium sulfate. Removal of solvent gave 7.95 g (98% yield) of product, melting point 54.7° C. by differential scanning calorimetry (DSC). Analysis on an NMR spectrometer was consistent with the desired product: $^1$H NMR (CDCl$_3$) aromatic protons 7.15–7.80 (m, 9H), methylene protons 3.71 (d, 2H), and SH 1.76 (t, 1H).

Example 4

Preparation of N-(2-Mercaptoethyl)-4-benzoylbenzamide (Compound II)

A photoactivatable chain transfer reagent of the present invention was prepared in the following manner, and used in the manner described in Examples 14–20. 2-Aminoethanethiol hydrochloride, 24.39 g (0.215 mol), was added to a 1 liter 3-neck flask and dissolved in 200 ml of chloroform under an argon atmosphere. A solution of 50.0 g (0.204 mol) of 4-benzoylbenzoyl chloride, prepared according to the general method described in Example 1, in 250 ml of chloroform was then added dropwise over a 45 minute period. The mixture was stirred overnight at room temperature. The product was washed with water and 0.1 N hydrochloric acid and then dried over sodium sulfate. Removal of solvent under reduced pressure yielded a slightly yellow solid product which was recrystallized twice from toluene to give 50.0 g of a white powder, an 86% yield. Melting point on this product was 112.9° C. by DSC. Analysis on an NMR spectrometer was consistent with the desired product: $^1$H NMR (CDCl$_3$) aromatic protons 7.20–7.85 (m, 9H), amide NH 6.70–7.05 (m, 1H), methylene adjacent to amide 3.55 (q, 2H), methylene adjacent to SH 2.55–3.00 (m, 2H), and SH 1.40 (t, 1H).

Example 5

Preparation of N-(2-Mercaptoethyl)-3,5-bis(4-benzoylbenzyloxy)benzamide (Compound III)

A photoactivatable chain transfer reagent of the present invention was prepared in the following manner, and used in the manner described in Examples 23–27. 3,5-Dihydroxybenzoic acid, 46.2 g (0.30 mol), was weighed into a 250 ml flask equipped with a Soxhlet extractor and condenser. Methanol, 48.6 ml, and concentrated sulfuric acid, 0.8 ml, were added to the flask and 48 g of 3A molecular sieves were placed in the Soxhlet extractor. The extractor was filled with methanol and the mixture was heated at reflux overnight. Gas chromatographic analysis of the resulting product showed a 98% conversion to the desired methyl ester. The solvent was removed under reduced pressure to give approximately 59 g of crude product. This product was used in the following step without further purification. A small sample was previously purified for NMR analysis, resulting in a spectrum consistent with the desired product: $^1$H NMR (DMSO-d$_6$) aromatic protons 6.75 (d, 2H) and 6.38 (t, 1H), methyl ester 3.75 (s, 3H).

The entire methyl ester product from above was placed in a 2 liter flask with overhead stirrer and condenser, followed by the addition of 173.25 g (0.63 mol) of 4-bromomethylbenzophenone, prepared according to the general method described in Example 2, 207 g (1.50 mol) of potassium carbonate, and 1200 ml of acetone. The resulting mixture was then refluxed overnight to give complete reaction as indicated by thin layer chromatography (TLC). The solids were removed by filtration and the acetone was evaporated under reduced pressure to give 49 g of crude product. The solids were diluted with 1 liter of water and extracted with 3×1 liter of chloroform. The extracts were combined with the acetone soluble fraction and dried over sodium sulfate, yielding 177 g of crude product. The product was recrystallized from acetonitrile to give 150.2 g of a white solid, a 90% yield for the first two steps. Melting point of the product was 131.5° C. (DSC) and analysis on an NMR spectrometer was consistent with the desired product: $^1$H NMR (CDCl$_3$) aromatic protons 7.25–7.80 (m, 18H), 7.15 (d, 2H), and 6.70 (t, 1H), benzylic protons 5.05 (s, 4H), and methyl ester 3.85 (s, 3H).

The methyl 3,5-bis(4-benzoylbenzyloxy)benzoate, 60.05 g (0.108 mol), was placed in a 2 liter flask, followed by the addition of 120 ml of water, 480 ml of methanol, and 6.48 g (0.162 mol) of sodium hydroxide. The mixture was heated at reflux for three hours to complete hydrolysis of the ester. After cooling, the methanol was removed under reduced pressure and the sodium salt of the acid was dissolved in 2400 ml of warm water. The acid was precipitated using concentrated hydrochloric acid, filtered, washed with water, and dried in a vacuum oven to give 58.2 g of a white solid (99% yield). Melting point on the product was 188.3° C.(DSC) and analysis on an NMR spectrometer was consistent with the desired product: $^1$H NMR (DMSO-d$_6$) aromatic protons 7.30–7.80 (m, 18H), 7.15 (d, 2H), and 6.90 (t, 1H), benzylic protons 5.22 (s, 4H).

The 3,5-bis(4-benzoylbenzyloxy)benzoic acid, 20.0 g (36.86 mmol), was added to a 250 ml flask, followed by 36 ml of toluene, 5.4 ml (74.0 mmol) of thionyl chloride, and 28 μl of N,N-dimethylformamide. The mixture was refluxed for four hours to form the acid chloride. After cooling, the solvent and excess thionyl chloride were removed under reduced pressure. Residual thionyl chloride was removed by four additional evaporations using 20 ml of chloroform each. The crude material was recrystallized from toluene to give 18.45 g of product, an 89% yield. Melting point on the product was 126.9° C. (DSC) and analysis on an NMR spectrometer was consistent with the desired product: $^1$H NMR (CDCl$_3$) aromatic protons 7.30–7.80 (m, 18H), 7.25 (d, 2H), and 6.85 (t, 1H), benzylic protons 5.10 (s, 4H).

The 2-aminoethanethiol hydrochloride, 4.19 g (36.7 mmol), was added to a 250 ml flask equipped with an overhead stirrer, followed by 15 ml of chloroform and 10.64 ml (76.5 mmol) of triethylamine. After cooling the amine solution on an ice bath, a solution of 3,5-bis(4-benzoylbenzyloxy)benzoyl chloride, 18.4 g (32.8 mmol), in 50 ml of chloroform was added dropwise over a 50 minute period. Cooling on ice was continued 30 minutes, followed by warming to room temperature for two hours. The product was diluted with 150 ml of chloroform and washed with 5×250 ml of 0.1 N hydrochloric acid. The product was dried over sodium sulfate and recrystallized twice from 15:1 toluene: hexane to give 13.3 g of product, a 67% yield. Melting point on the product was 115.9° C. (DSC) and analysis on an NMR spectrometer was consistent with the desired product: $^1$H NMR (DMSO-d$_6$) aromatic protons 7.20–7.80 (m, 18H), 6.98 (d, 2H), and 6.65 (t, 1H), amide NH 6.55 (broad t, 1H), benzylic protons 5.10 (s, 4H), methylene adjacent to amide N 3.52 (q, 2H), methylene adjacent to SH 2.70 (q, 2H), and SH 1.38 (t, 1H).

Example 6

Preparation of N-(2-Mercaptoethyl)-2.6-bis(4-benzoylbenzamido)hexanamide (Compound IV)

A photoactivatable chain transfer reagent of the present invention was prepared in the following manner, and used in the manner described in Example 21. Lysine monohydrochloride, 3.65 g (20 mmol), was dissolved in 8 ml of 2 N sodium hydroxide and cooled in an ice bath. A solution of 10.77 g (44 mmol) 4-benzoylbenzoyl chloride, prepared according to the general method described in Example 1, in 17 ml of chloroform was added simultaneously with 4.48 g of sodium hydroxide in 19 ml of water. The reaction was stirred on the ice bath for 2 hours and then was allowed to warm to room temperature for 3 hours. Hydrochloric acid was used to adjust the pH to 1 and an additional 60 ml of chloroform were added. A centrifuge was used to separate the layers and the aqueous was extracted with 3×50 ml of chloroform. The combined organic extracts were dried over sodium sulfate. An attempt was made to recrystallize the resulting solid product from 80% acetic acid but the recovery of product was poor. The mother liquors were diluted with water to precipitate the product, which was then dissolved in chloroform, washed with 10% sodium bicarbonate, 1 N hydrochloric acid, and finally water. The solution was dried over sodium sulfate and the product was used without purification. Analysis on an NMR spectrometer was consistent with the desired product: $^1$H NMR (CDCl$_3$) acid proton 8.45 (broad s, 1H), aromatic and amide protons 7.00–8.10 (m, 20H), CH 4.50–4.90 (m, 1H), methylene adjacent to N 3.30–3.70 (m, 2H), remaining methylenes 1.10–2.25 (m, 6H).

The lysine derivative, 4.35 g (7.73 mmol), and N-hydroxysuccinimide, 0.901 g (7.83 mmol), were dissolved in 40 ml of dry 1,4-dioxane, followed by the addition of 1.951 g (9.45 mmol) of 1,3-dicyclohexylcarbodiimide (DCC) in 10 ml of 1,4-dioxane. The mixture was allowed to stir overnight at room temperature. The resulting white solid was filtered off and washed with 2×25 ml of 1,4-dioxane. The solvent was removed under reduced pressure and the residue was rinsed with 3×25 ml of hexane to remove excess DCC. The resulting N-oxysuccinimide (NOS) ester, 4.10 g (81% yield), was used without further purification.

2-Aminoethanethiol hydrochloride, 0.75 g (6.6 mmol), was diluted with 15 ml of chloroform and 1.09 ml of triethylamine under an argon atmosphere. The NOS ester, 4.10 g (6.22 mmol), in 25 ml of chloroform was added dropwise at room temperature over a 30 minute period. After 4 hours of reaction, the mixture was washed with water and 0.05 N hydrochloric acid, followed by drying over sodium sulfate. The product was purified using silica gel flash chromatography using a 95:5 CHCl$_3$: CH$_3$OH solvent system to give 2.30 g of product, a 59% yield. Analysis on an NMR spectrometer was consistent with the desired product: $^1$H NMR (CDCl$_3$) aromatic and amide protons 6.90–8.00 (m, 21H), CH 4.40–4.85 (m, 1H), methylenes adjacent to N 3.00–3.75 (m, 4H), remaining methylenes 1.00–2.95 (m, 8H), and SH 1.40 (t, 1H).

Example 7

Preparation of N,N-Bis[2-(4-benzoylbenzyloxy) ethyl]-4-mercaptobutanamide (Compound V)

A photoactivatable chain transfer reagent of the present invention was prepared in the following manner, and used in the manner described in Example 22. Diethanolamine, 5.43 g (51.7 mmol), was diluted with 50 ml of dichloromethane in a 100 ml flask, followed by the dropwise addition of 11.3 g (51.7 mmol) of di-t-butyldicarbonate in 10 ml of dichloromethane. The mixture was allowed to stir two hours at room temperature. The volatiles were removed under reduced pressure and the residue was dissolved in 45 ml of chloroform. The product was washed with the following solutions of sodium hydroxide: 2×45 ml of 1 N, 45 ml of 0.1 N, and 45 ml of 0.01 N. The aqueous washes were back-extracted with 3×45 ml chloroform and the combined organic extracts were dried over sodium sulfate. The product was purified by silica gel flash chromatography using an ethyl acetate solvent to give 6.74 g of a viscous oil, a 63% yield. Analysis on an NMR spectrometer was consistent with the desired product: $^1$H NMR (CDCl$_3$) hydroxyl protons and methylenes adjacent to oxygen 3.50–3.85 (m, 6H), methylenes adjacent to nitrogen 3.25–3.50 (m, 4H), and t-butyl 1.45 (s, 9H).

The t-BOC diethanolamine, 6.7 g (32.6 mmol), was placed in a 100 ml flask equipped with an overhead stirrer, followed by the addition of 50 ml of dry tetrahydrofuran, 19.72 g (71.7 mmol) of 4-bromomethylbenzophenone prepared according to the general method described in Example 2, 1.75 g (5.43 mmol) of tetra-n-butylammonium bromide, and 0.083 g (0.55 mmol) of sodium iodide. Sodium hydride, 3.1 g (71.7 mmol) of 55% in mineral oil, was added portionwise to the solution until approximately 80% of the total had been added. The mixture was stirred overnight at room temperature under an argon atmosphere. The remaining 20% of the sodium hydride was then added and stirring was continued for an additional hour. The mixture was diluted with 200 ml of water and was extracted with 3×100 ml of chloroform. The combined organic extracts were washed with 2×100 ml portions of water and dried over sodium sulfate. The product was purified by silica gel flash chromatography using 95:5 chloroform:acetonitrile to give 15.6 g of product, an 81% yield. Analysis on an NMR spectrometer was consistent with the desired product: $^1$H NMR (CDCl$_3$) aromatic protons 7.10–7.80 (m, 18H), benzylic protons 4.53 (s, 4H), methylene protons 3.30–3.75 (m, 8H), and t-butyl 1.45 (s, 9H).

The alkylated t-BOC compound, 1.90 g (3.20 mmol), was dissolved in 20 ml of ethyl acetate and 10 ml of concentrated hydrochloric acid. After stirring for 10 minutes at room temperature, the solution was treated with a mixture of 40 ml of chloroform, 20 ml of water, and 30 ml of 6 N sodium hydroxide. The organic layer was removed and the aqueous was extracted with 2×20 ml of chloroform. The combined organic extracts were then dried over sodium sulfate and the solvent was removed to give 1.4 g of crude product. This residue was diluted with 7 ml of acetonitrile, followed by the addition of 0.346 g (3.39 mmol) γ-thiobutyrolactone and purging of the solution with argon. The mixture was stirred overnight at 80° C. followed by purification on a silica gel flash chromatography column using 85:15 chloroform:acetonitrile to give 0.51 g of product, a 27% yield. Analysis on an NMR spectrometer was consistent with the desired product: $^1$H NMR (CDCl$_3$) aromatic protons 7.10–7.80 (m, 18H), benzylic protons 4.50 (s, 4H), methylenes adjacent to nitrogen and oxygen, 3.60 (broad s, 8H), methylenes adjacent to carbonyl and sulfur 2.30–2.70 (m, 4H), methylene 1.60–2.10 (m, 2H), and SH 1.25 (t, 1H).

Example 8

Preparation of N-(2-Mercaptoethyl)-3,4,5-tris(4-benzoylbenzyloxy)benzamide (Compound VI)

A photoactivatable chain transfer reagent of the present invention was prepared in the following manner, and used in the manner described in Example 28. Gallic acid, 10.0 g (58.8 mmol), was added to a 250 ml flask, followed by 100 ml of methanol and 10 ml of concentrated sulfuric acid. The mixture was refluxed for 30 minutes, followed by removal of solvent under reduced pressure. An additional 100 ml of methanol were added and the mixture was refluxed for 30 minutes and evaporated again. This process was repeated a third time to complete formation of the methyl ester. The residue was diluted with 500 ml of ethyl acetate and was washed with 2×500 ml of cold water. The water washes were back-extracted with 500 ml of ethyl acetate and the combined extracts were dried over sodium sulfate. Removal of solvent gave 9.9 g of a white solid for a 92% yield. Analysis on an NMR spectrometer was consistent with the desired product: $^1$H NMR (DMSO-d$_6$) phenolic protons 8.50–9.20 (broad m, 3H), aromatic protons 6.85 (s, 2H), and CH$_3$ 3.70 (s, 3H).

Methyl gallate, 9.21 g (0.050 mol), was added to a 1 liter flask equipped with overhead stirrer and reflux condenser, followed by the addition of 400 ml of 2-propanol, 0.31 g (2.1 mmol) of sodium iodide, and 41.25 g (0.15 mol) of 4-bromomethylbenzophenone, prepared according to the general method described in Example 2. After heating to reflux, 100 ml of 2 M sodium hydroxide were added in 5 ml portions over a 20 minute period. An additional 200 ml of 2-propanol were added to permit adequate stirring. After refluxing for 2.5 hours, the mixture was cooled and filtered to remove the solids. The solid was resuspended in 800 ml of water and filtered a total of three times to remove inorganic salts and then was dried to give 34.2 g of crude product (89% yield). Analysis on an NMR spectrometer was consistent with the desired product: $^1$H NMR (CDCl$_3$) aromatic protons 7.10–7.80 (m, 29H), benzylic protons 5.15 (s, 6H), and CH$_3$ 3.80 (s, 3H). This product was used without further purification.

Methyl 3,4,5-tris(4-benzoylbenzyloxy)benzoate, 15.34 g (20.0 mmol), was added to a 500 ml flask and dissolved in 125 ml of tetrahydrofuran with heating. To the refluxing solution was added 12 ml of 2 M potassium hydroxide and the reflux was continued for 35 hours. After cooling, the mixture was diluted with 440 ml of water and acidified with concentrated hydrochloric acid. The product was extracted with 5×500 ml of ethyl acetate and the combined organic extracts were dried over sodium sulfate. Removal of solvent gave 13.40 g of a solid, purified by recrystallization from a mixture of 300 ml of chloroform and 120 ml of hexane. After filtration and drying, 8.0 g of product were isolated for a 53% yield. Analysis on an NMR spectrometer was consistent with the desired product: $^1$H NMR (DMSO-d$_6$) aromatic protons 7.05–7.90 (m, 29H) and benzylic protons 5.05–5.35 (m, 6H).

3,4,5-Tris(4-benzoylbenzyloxy)benzoic acid, 0.50 g (0.664 mmol), was added to a 50 ml flask, followed by 0.092 g (0.80 mmol) of N-hydroxysuccinimide and 3 ml of dry 1,4-dioxane. The mixture was placed under argon and heated to reflux. A solution of 0.206 g (1.0 mmol) of DCC in 5 ml of 1,4-dioxane was then added dropwise over a 25 minute period. Reflux was continued for 1.5 hours and the mixture was then heated overnight at 60° C. The mixture was cooled to room temperature, filtered to remove solids, and then evaporated under reduced pressure. The residue was extracted with 2×4 ml of hexane and then dried under reduced pressure to provide 0.56 g of crude product. No further purification of this NOS ester was performed before use in the following step.

Aminoethanethiol hydrochloride, 0.083 g (0.73 mmol), was added to a 50 ml flask, followed by 4 ml of chloroform and 0.14 ml of triethylamine. While stirring under an argon atmosphere, a solution of 0.56 g (0.66 mmol) of the NOS ester in 4 ml of chloroform was added over a 30 minute period. The reaction was stirred overnight under argon at room temperature. The mixture was washed with 0.1 N hydrochloric acid and dried over sodium sulfate. The product was purified on a silica gel flash chromatography column using a 90:10 chloroform:acetonitrile solvent system to give 0.200 g of product, a 37% yield. Analysis on an NMR spectrometer was consistent with the desired product: $^1$H NMR (CDCl$_3$) aromatic protons 7.00–7.80 (m, 29H), amide proton 6.65 (broad t, 1H), benzylic protons 5.15 (s, 6H), methylene adjacent to nitrogen 3.50 (q, 2H), methylene adjacent to sulfur 2.70 (q, 2H), and SH 1.35 (t, 1H).

Example 9

Preparation of 1,4-Bis(4-benzoylbenzyloxy)-2-mercaptobutane (Compound VII)

A photoactivatable chain transfer reagent of the present invention was prepared in the following manner, and used in the manner described in Example 29. 2-Butene-1,4-diol (95% cis), 5.02 g (56.97 mmol), was added to a 250 ml flask and diluted with 100 ml of dry THF. Sodium hydride, 3.0 g of 60% in mineral oil (125 mmol), was then added, followed by the addition of 32.90 g (119.6 mmol) of 4-bromomethylbenzophenone, prepared according to the general method described in Example 2. The mixture was stirred overnight at room temperature under an argon atmosphere. The product was quenched carefully with water, diluted with chloroform, and the organic layer was separated and dried over sodium sulfate. The crude product was purified initially by silica gel flash chromatography using a chloroform:acetonitrile:acetic acid 95:4:1 solvent system. This partially purified product was subjected to two additional silica gel flash chromatography purifications using a chloroform:acetonitrile 95:5 solvent to give a final yield of 18.52 g (68%). Analysis on an NMR spectrometer was consistent with the desired product: $^1$H NMR (CDCl$_3$) aromatic protons 7.00–7.90 (m, 18H), vinyl protons 5.65–5.90 (m, 2H), benzylic protons 4.55 (s, 4H), and allylic protons 4.10 (d, 4H).

The 1,4-bis(4-benzoylbenzyloxy)-2-butene, 2.07 g (4.34 mmol), was diluted with 10 ml of THF, followed by the addition of 0.35 g (4.60 mmol) of thiolacetic acid and 0.082 g (0.5 mmol) of 2,2'-azobisisobutyronitrile (AIBN). The solution was deoxygenated with an argon sparge for 5 minutes and was heated overnight at 55° C. at which time NMR showed approximately 25% reaction. An additional 0.35 g of thiolacetic acid and 0.41 g of AIBN were added and the heating was continued overnight. NMR analysis at that time showed approximately 70% reaction so an additional 0.35 g of thiolacetic acid and 0.41 g of AIBN were added and the heating was continued for 5.5 hours. The solvent was then evaporated and the product was purified on a silica gel flash chromatography column using chloroform with an increasing gradient of acetonitrile of 0, 1, and 2%. A total of 0.971 g of product were isolated for a 40% yield. NMR analysis (CDCl$_3$) confirmed the presence of the thioester group with the acetate methyl group at 2.30 ppm. This analysis also confirmed the presence of some starting olefin along with AIBN decomposition products. A portion of this product, 100 mg, was treated with 1 ml of 0.38 M potassium hydroxide in methanol under argon. After heating at 50° C. for three minutes, the solution was treated with 1 ml of 1 N hydrochloric acid and the product was extracted with 3×3 ml of chloroform. The product was dried over sodium sulfate and evaporated to give 86.5 mg. NMR analysis (CDCl$_3$) confirmed the removal of the acetate group with the absence of the singlet at 2.30 ppm and the presence of the sulfhydryl with a doublet at 1.25 ppm. The purity was estimated at 80% and the compound was used without further purification.

Example 10

Preparation of N-(2-Mercaptoethyl)-4-[4-(3,3,4,4,5,5,6,6,7,7,8,8,9,9,10,10, 10-heptadecafluoro-2-thiadecyl)benzoyl]benzamide (Compound VIII)

A photoactivatable chain transfer reagent of the present invention is prepared in the following manner, and used in the manner described in Example 30. Terephthalic acid chloride-mono methyl ester, 5.00 g (25.2 mmol), is dissolved in 50 ml of anhydrous toluene, followed by the addition of 8.89 g (66.7 mmol) of aluminum chloride. The resulting mixture is warmed at 40° C.for four hours and then is quenched by the addition of water. The product is extracted with chloroform and dried over sodium sulfate, followed by purification with silica gel flash chromatography.

The methyl 4-(4-methylbenzoyl)benzoate, 2.0 g (7.87 mmol), is dissolved in 80 ml of carbon tetrachloride, followed by the addition of 20 mg of dibenzoyl peroxide and 1.51 g (9.45 mmol) of Br$_2$. The mixture is heated at reflux and is monitored by gas chromatography until the starting material is largely consumed and the quantity of dibromo product is minimal. The product is then washed with sodium bisulfite to remove any excess bromine and dried over sodium sulfate. The final product is purified by recrystallization from an appropriate solvent system.

The methyl 4-(4-bromomethylbenzoyl)benzoate, 0.50 g (1.50 mmol), is dissolved in 10 ml of ethanol along with 0.114 g (1.50 mmol) of thiourea. The mixture is heated at 50° C. with formation of a solid product. The solid is isolated by filtration, washed, and then treated with aqueous sodium hydroxide. After heating at 80° C. until the reaction is complete, the cooled solution is treated with dilute hydrochloric acid until acidic. The precipitated product is isolated by filtration and purified by recrystallization from an appropriate solvent system.

The 4-(4-mercaptomethylbenzoyl)benzoic acid, 0.50 g (1.84 mmol), is dissolved in 10 ml of dry N,N-dimethylformamide (DMF), followed by the addition of 1.00 g (1.84 mmol) of perfluorooctyl iodide and 0.227 g (4.05 mmol) of potassium hydroxide. The reaction is sealed under argon and warmed gently until thin layer chromatography shows consumption of starting material. The mixture is diluted with water, acidified with dilute hydrochloric acid, and extracted with chloroform. The final product is purified using silica gel flash chromatography.

The perfluoro substituted acid, 1.00 g (1.45 mmol), is diluted with 10 ml of thionyl chloride, and after the addition of 0.050 ml of DMF, is heated at reflux for 4 hours to convert the acid to the corresponding acid chloride. The excess thionyl chloride is then removed under reduced pressure using repeated evaporations with chloroform to help remove the last traces. The acid chloride is diluted with 10 ml of chloroform and cooled to 0° C., followed by the addition of 0.405 g (4.0 mmol) of triethylamine and 0.181 g (1.60 mmol) of 2-aminoethanethiol hydrochloride. After warming to room temperature, the mixture is stirred until the starting acid chloride is consumed. The mixture is then diluted with chloroform, washed with dilute hydrochloric acid, and dried over sodium sulfate. The resulting product is purified by silica gel flash chromatography.

Example 11

Preparation of N-Succinimidyl 6-Maleimidohexanoate

A functionalized monomer was prepared in the following manner, and was used in the manner described in Examples 15 and 25 to introduce activated ester groups to the backbone of a polymer. 6-Aminohexanoic acid, 100.0 g (0.762 moles), was dissolved in 300 ml of acetic acid in a three-neck, 3 liter flask equipped with an overhead stirrer and drying tube. Maleic anhydride, 78.5 g (0.801 moles), was dissolved in 200 ml of acetic acid and added to the 6-aminohexanoic acid solution. The mixture was stirred one hour while heating on a boiling water bath, resulting in the formation of a white solid. After cooling overnight at room temperature, the solid was collected by filtration and rinsed with 2×50 ml of hexane. After drying, the typical yield of the (Z)-4-oxo-5-aza-2-undecendioic acid was 158–165 g (90–95%) with a melting point of 160–165° C. Analysis on an NMR spectrometer was consistent with the desired product: $^1$H NMR (DMSO-d$_6$) amide proton 8.65–9.05 (m, 1H), vinyl protons 6.10, 6.30 (d, 2H), methylene adjacent to nitrogen 2.85–3.25 (m, 2H), methylene adjacent to carbonyl 2.15 (t, 2H), and remaining methylenes 1.00–1.75 (m, 6H).

(Z)-4-Oxo-5-aza-2-undecendioic acid, 150.0 g (0.654 moles), acetic anhydride, 68 ml (73.5 g, 0.721 moles), and phenothiazine, 500 mg, were added to a 2 liter three-neck round bottom flask equipped with an overhead stirrer. Triethylamine, 91 ml (0.653 moles), and 600 ml of THF were added and the mixture was heated to reflux while stirring. After a total of 4 hours of reflux, the dark mixture was cooled to <60° C. and poured into a solution of 250 ml of 12 N HCl in 3 liters of water. The mixture was stirred 3 hours at room temperature and then was filtered through a Celite 545 pad to remove solids. The filtrate was extracted with 4×500 ml of chloroform and the combined extracts were dried over sodium sulfate. After adding 15 mg of phenothiazine to prevent polymerization, the solvent was removed under reduced pressure. The 6-maleimidohexanoic acid was recrystallized from 2:1 hexane:chloroform to give typical yields of 76–83 g (55–60%) with a melting point of 81–85° C. Analysis on an NMR spectrometer was consistent with the desired product: $^1$H NMR (CDCl$_3$) maleimide protons 6.55 (s, 2H), methylene adjacent to nitrogen 3.40 (t, 2H), methylene adjacent to carbonyl 2.30 (t, 2H), and remaining methylenes 1.05–1.85 (m, 6H).

The 6-maleimidohexanoic acid, 20.0 g (94.7 mmol), was dissolved in 100 ml of chloroform under an argon atmosphere, followed by the addition of 41 ml (0.47 mol) of oxalyl chloride. After stirring for 2 hours at room temperature, the solvent was removed under reduced pressure with 4×25 ml of additional chloroform used to remove the last of the excess oxalyl chloride. The acid chloride was dissolved in 100 ml of chloroform, followed by the addition of 12.0 g (0.104 mol) of N-hydroxysuccinimide and 16.0 ml (0.114 mol) of triethylamine. After stirring overnight at room temperature, the product was washed with 4×100 ml of water and dried over sodium sulfate. Removal of solvent gave 24.0 g of product (82%) which was used without further purification. Analysis on an NMR spectrometer was consistent with the desired product: $^1$H NMR (CDCl$_3$) maleimide protons 6.60 (s, 2H), methylene adjacent to nitrogen 3.45 (t, 2H), succinimidyl protons 2.80 (s, 4H), methylene adjacent to carbonyl 2.55 (t, 2H), and remaining methylenes 1.15–2.00 (m, 6H).

Example 12

Preparation of 5-Maleimidopentyl Isocyanate

A heterobifunctional molecule was prepared in the manner described below. The molecule was used in the manner described in Example 17 to derivatize polymers in order to introduce maleimide groups, which in turn, can be used to immobilize molecules containing SH groups. The 6-maleimidohexanoic acid, 50.0 g (0.237 mol), prepared according to the general method described in Example 11, was dissolved in 250 ml of chloroform, followed by the addition of 100.0 ml (1.146 mol) of oxalyl chloride under an argon atmosphere. After stirring overnight at room temperature, the solvent was removed under reduced pressure with 4×50 ml of additional chloroform used to remove the last of the excess oxalyl chloride. The acid chloride was dissolved in 100 ml of acetone, followed by the addition of 23.0 g (0.354 mol) of sodium azide in 100 ml of water at 0° C. After stirring 1 hour on an ice bath, the product was extracted with 2×250 ml of ethyl acetate. The extracts were dried over sodium sulfate and the solvent was removed under reduced pressure while keeping the temperature below 25° C. The presence of the acyl azide group was confirmed by IR (2130 cm$^{-1}$) and the product was stored in a freezer.

The entire acyl azide sample was dissolved in 500 ml of chloroform and was heated to reflux for a total of 3.5 hours to convert the compound to the isocyanate. Removal of solvent gave 40.0 g of product for an 81% yield. The presence of the isocyanate group was confirmed by IR (2275 cm$^{-1}$). The product was used without further purification.

Example 13

Polyacrylamide using 4-Mercaptomethylbenzophenone

A photoactivatable polymer of the present invention was prepared in the following manner. Acrylamide, 4.763 g (67.0 mmol), was dissolved in 61.6 ml of DMSO, followed by 0.517 g (3.15 mmol) of AIBN, and 0.226 g (0.99 mmol) of 4-mercaptomethylbenzophenone, prepared according to the general method described in Example 3. The solution was deoxygenated with a helium sparge for 5 minutes, sealed under argon, and heated overnight at 55° C. The polymer solution was added with stirring to 600 ml of ether to precipitate the polymer. After decanting the solvent, the solid was washed with 300 ml of ether and 2×300 ml of chloroform. After drying under vacuum, 5.24 g of product were isolated.

Example 14

Polyacrylamide using N-(2-Mercaptoethyl)-4-benzoylbenzamide

A photoactivatable polymer of the present invention was prepared in the following manner. Acrylamide, 8.575 g (120.6 mmol), was dissolved in 102.7 ml of DMSO, followed by 7.921 g (48.2 mmol) of AIBN, and 1.425 g (5.0 mmol) of N-(2-mercaptoethyl)-4-benzoylbenzamide, prepared according to the general method described in Example 4. The solution was deoxygenated with a helium sparge for 5 minutes, sealed under argon, and heated overnight at 55° C. The polymer solution was added with stirring to 1000 ml of acetone to precipitate the polymer. The solid was isolated and resuspended for 1 hour in 500 ml of acetone, followed by filtration and vacuum drying to give 9.5 g product. The resultant polymer has the general structure:

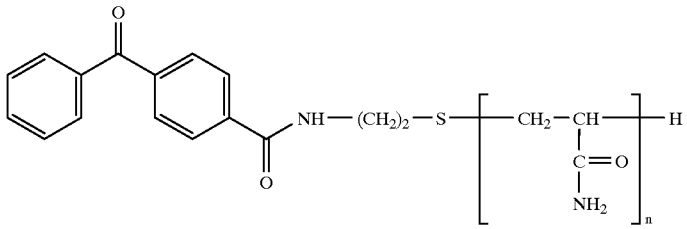

Similar procedures were conducted using tetrahydrofuran as solvent. In this case, the polymers precipitated during the polymerization process and were isolated by filtration and rinsing with tetrahydrofuran.

Example 15

Copolymer of Acrylamide and N-Succinimidyl 6-Maleimidohexanoate using N-(2-Mercaptoethyl)-4-benzoylbenzamide A photoactivatable copolymer of the present invention was prepared in the following manner. Acrylamide, 7.896 g (111.0 mmol), was dissolved in 107.6 ml of DMSO, followed by 0.285 g (1.00 mmol) of N-(2-mercaptoethyl)-4-benzoylbenzamide, prepared according to the general method described in Example 4, 1.818 g (5.9 mmol) of N-succinimidyl 6-maleimidohexanoate, prepared according to the general method described in Example 11, 0.328 g (2.0 mmol) of AIBN, and 0.108 ml of N,N,N',N'-tetramethylethylenediamine (TEMED). The solution was deoxygenated with a helium sparge for 4 minutes, followed by an argon sparge for an additional 4 minutes. The sealed vessel was then heated overnight at 55° C. to complete the polymerization. The polymer was precipitated by pouring the solution into 300 ml of ether and the resulting solid was isolated by filtration and resuspended in 300 ml of chloroform. The final product was recovered by filtration and dried in a vacuum oven to provide 9.85 g of solid.

Example 16

Copolymer of N-Vinylpyrrolidone and 3-Allyloxy-1,2-propanediol using N-(2-Mercaptoethyl)-4-benzoylbenzamide—Oxidation to Aldehyde A photoactivatable copolymer of the present invention was prepared in the following manner. N-Vinylpyrrolidone, 1.80 g (16.2 mmol), was diluted with 2.5 ml of DMSO, followed by the addition of 0.213 g (1.61 mmol) of 3-allyloxy-1,2-propanediol, 0.20 g (1.22 mmol) of AIBN, 0.050 ml of TEMED, and 0.060 g (0.21 mmol) of N-(2-mercaptoethyl)-4-benzoylbenzamide, prepared according to the general method described in Example 4. The solution was deoxygenated with a nitrogen sparge for 5 minutes and the sealed vessel was then heated at 55° C. overnight. The resulting product was dialyzed against deionized water using 6,000–8,000 molecular weight cutoff tubing. A portion of the resulting solution, 5 ml, was removed as a retained sample of the diol polymer and 1.18 g (5.5 mmol) of sodium periodate were added to the remaining 55 ml of solution. After an overnight oxidation at room temperature, the product was again dialyzed against deionized water (6,000–8,000 MWCO). Lyophilization of the final product gave 1.25 g of solid.

Example 17

Copolymer of Acrylamide and N-(3-Aminopropyl) methacrylamide Hydrochloride using N-(2-Mercaptoethyl)-4-benzoylbenzamide—Conversion to Maleimide Derivative A photoactivatable copolymer of the present invention was prepared in the following manner. Acrylamide, 4.282 g (60.2 mmol), was dissolved in 58 ml of DMSO, followed by 0.436 g (2.7 mmol) of AIBN, 0.340 g (1.9 mmol) of N-(3-aminopropyl)methacrylamide hydrochloride, and 0.378 g (1.3 mmol) of N-(2-mercaptoethyl)-4-benzoylbenzamide, prepared according to the general method described in Example 4. The solution was deoxygenated with a helium sparge for 4 minutes, followed by an argon sparge for an additional 4 minutes. The sealed vessel was then heated overnight at 55° C. to complete the polymerization.

One-half of the DMSO solution, theoretically containing 0.95 mmol of primary amine in the polymer, was then slowly added to a solution of 1.12 g (4.75 mmol) of 5-maleimidopentyl isocyanate, prepared according to the general method described in Example 12, in 20 ml of dry DMSO. The solution was stirred overnight at room temperature and precipitated using ether. After washing with chloroform and drying in a vacuum oven, 2.875 g of polymer were obtained. The presence of maleimide in the polymer was confirmed by the presence of a broad singlet at 6.85 in the NMR (DMSO-$d_6$).

Example 18

Polyvinylphosphonic Acid using N-(2-Mercaptoethyl)-4-benzoylbenzamide

A photoactivatable polymer of the present invention was prepared in the following manner. Vinylphosphonic acid, 2.829 g (26.2 mmol), was dissolved in 3.3 ml of ethyl acetate, followed by 0.296 g (1.8 mmol) of AIBN, and 0.171 g (0.6 mmol) of N-(2-mercaptoethyl)-4-benzoylbenzamide, prepared according to the general method described in Example 4. The solution was deoxygenated with a helium sparge for 10 minutes, followed by an argon sparge for 2 minutes. The sealed vessel was then heated overnight at 55° C. to complete the polymerization. The precipitated polymer was then isolated by filtration and washed with additional ethyl acetate. Vacuum drying of the product gave 2.90 g of the polyvinylphosphonic acid.

Example 19

Copolymer of Acrylamide and 2-Vinyl-4,4-dimethyl-2-oxazolin-5-one using N-(2-Mercaptoethyl)-4-benzoylbenzamide A photoactivatable copolymer of the present invention was prepared in the following manner. Acrylamide, 1.0 g (14.1 mmol), was dissolved in 5 ml of tetrahydrofuran (THF), followed by the addition 0.066 g (0.24 mmol) of AIBN, 0.050 ml of TEMED, 0.220 g (1.58 mmol) of 2-vinyl-4,4-dimethyl-2-oxazolin-5-one, and 0.035 g (0.122 mmol) of N-(2-mercaptoethyl)-4-benzoylbenzamide, prepared according to the general method described in Example 4. The solution was deoxygenated with a nitrogen sparge for 5 minutes and the sealed vessel was heated at 55° C. overnight. The polymer precipitated from the ThF solution during polymerization and was isolated by filtration. After washing with additional THF, the polymer was dried to give 1.44 g of product.

Example 20

Copolymer of Acrolein and N-Vinylpyrrolidone using N-(2-Mercaptoethyl)-4-benzoylbenzamide A photoactivatable copolymer of the present invention was prepared in the following manner. N-Vinylpyrrolidone, 0.855 g (7.69 mmol), was dissolved in 1.4 ml of DMSO, followed by 0.110 g (1.96 mmol) of acrolein, 0.041 g (0.25 mmol) of AIBN, and 0.036 g (0.13 mmol) of N-(2-mercaptoethyl)-4-benzoylbenzamide, prepared according to the general method described in Example 4. The solution was deoxygenated with a helium sparge for 5 minutes, followed by an argon sparge for 5 minutes. The sealed vessel was then heated overnight at 55° C. to complete the polymerization. Chloroform, 10 ml, was added to each sample and the resulting solution was poured into 100 ml of ether to precipitate the polymer. The suspension was centrifuged to isolate the solid polymer. The solid was rinsed with 50 ml of ether and was redissolved in 10 ml of chloroform. The polymer was precipitated a second time by pouring into 100 ml of chloroform, followed by isolation by centrifuging. After vacuum drying of the product, 0.730 g of product were isolated. The presence of aldehyde in the polymer was confirmed by a broad doublet at 9.40 (DMSO-$d_6$) in the NMR spectrum.

Example 21

Polyacrylamide using N-(2-Mercaptoethyl)-2.6-bis (4-benzoylbenzamido)hexanamide

A photoactivatable polymer of the present invention was prepared in the following manner. Acrylamide, 0.939 g (13.2 mmol), was dissolved in 12.1 ml of DMSO, followed by the addition of 0.054 g (0.30 mmol) of AIBN and 0.061 g (0.10 mmol) of N-(2-mercaptoethyl)-2,6-bis(4-benzoylbenzamido)hexanamide, prepared according to the general method described in Example 6. The solution was deoxygenated with a helium sparge for 5 minutes and sealed under an argon atmosphere. The sealed vessel was heated at 55° C. overnight. The polymer was precipitated by pouring the DMSO solution into 120 ml of ether. The resulting solid was washed with 3×50 ml of chloroform and then vacuum dried to give 0.93 g of a white solid.

Example 22

Polyacrylamide using N,N-Bis[2-(4-benzoylbenzyloxy)ethyl]-4-mercaptobutanamide

A photoactivatable polymer of the present invention was prepared in the following manner. Acrylamide, 2.86 g (40.2 mmol), was dissolved in 36.7 ml of DMSO, followed by the addition of 0.165 g (1.0 mmol) of AIBN and 0.50 g (0.8 mmol) of N,N-bis[2-(4-benzoylbenzyloxy)ethyl]-4-mercaptobutanamide, prepared according to the general method described in Example 7. The solution was deoxygenated with a helium sparge for 5 minutes, followed by an argon sparge for 5 minutes. The sealed vessel was then heated overnight at 55° C. to complete the polymerization. The polymer was precipitated by addition of the DMSO solution to 400 ml of methanol. The solid was separated by centrifuging and was resuspended in 380 ml of fresh methanol. Centrifuging and vacuum drying gave 3.35 g of a white solid.

Example 23

Polyacrylamide using N-(2-Mercaptoethyl)-3,5-bis (4-benzoylbenzyloxy)benzamide

A photoactivatable polymer of the present invention was prepared in the following manner. Acrylamide, 0.850 (11.9 mmol), was dissolved in 10.9 ml of DMSO, followed by the addition of 0.049 g (0.30 mmol) of AIBN and 0.150 g (0.30 mmol) of N-(2-mercaptoethyl)-3,5-bis(4-benzoylbenzyloxy)benzamide, prepared according to the general method described in Example 5. The solution was deoxygenated with a helium sparge for 10 minutes and then was sealed under an argon atmosphere. The sealed vessel was then heated overnight at 55° C. to complete the polymerization. The polymer was precipitated by pouring the DMSO solution into 50 ml of methanol with stirring. The solid was separated by centrifuging and was washed with 2×50 ml of methanol and dried under vacuum to give 0.85 g of product.

Example 24

Polyvinylpyrrolidone using N-(2-Mercaptoethyl)-3, 5-bis(4-benzoylbenzyloxy)benzamide A photoactivatable polymer of the present invention was prepared in the following manner. N-Vinylpyrrolidone, 9.248 g (83.2 mmol), was diluted with 10.4 ml of DMSO, followed by the addition of 0.411 g (2.5 mmol) of AIBN and 0.752 g (1.3 mmol) of N-(2-mercaptoethyl)-3,5-bis(4-benzoylbenzyloxy)benzamide, prepared according to the general method described in Example 5. The solution was deoxygenated with a helium sparge for 5 minutes, followed by an argon sparge for 5 minutes. The sealed vessel was then heated overnight at 55° C. to complete the polymerization. The solution was then dialyzed against deionized water using 6,000–8,000 molecular weight cutoff tubing for 5 days. The product was lyophilized to give 9.01 g of a white solid.

Example 25

Copolymer of Acrylamide and N-Succinimidyl 6-Maleimidohexanoate using of N-(2-Mercaptoethyl)-3,5-bis(4-benzoylbenzyloxy)benzamide A photoactivatable copolymer of the present invention was prepared in the following manner. Acrylamide, 7.639 g (107.4 mmol), was dissolved in 104 ml of THF, followed by 0.328 g (2.0 mmol) of AIBN, 0.104 ml of TEMED, 0.602 g (1.00 mmol) of N-(2-mercaptoethyl)-3,5-bis(4-benzoylbenzyloxy)benzamide, prepared according to the general method described in Example 5, and 1.76 g (5.7 mmol) of N-succinimidyl 6-maleimidohexanoate, prepared according to the general method described in Example 11. The solution was deoxygenated with a helium sparge for 4 minutes, followed by an argon sparge for an additional 4 minutes. The sealed vessel was then heated overnight at 55° C. to complete the polymerization. The precipitated polymer was isolated by filtration and was washed by stirring in 100 ml of THF for 30 minutes. The final product was recovered by filtration and dried in a vacuum oven to provide 8.96 g of solid.

Example 26

Copolymer of N-Vinylpyrrolidone and 3-Allyloxy-1,2-propanediol using N-(2-Mercaptoethyl)-3,5-bis (4-benzoylbenzyloxy)benzamide—Oxidation to Aldehyde A photoactivatable copolymer of the present invention was prepared in the following manner. N-Vinylpyrrolidone, 16.58 g (0.149 mol), was dissolved in 21.0 ml of DMSO followed by 2.218 g (16.8 mmol) of 3-allyloxy-1,2-propanediol, 0.985 g (6.0 mmol) of AIBN, 0.18 ml of TEMED, and 1.203 g (2.0 mmol) of N-(2-mercaptoethyl)-3,5-bis(4-benzoylbenzyloxy)benzamide, prepared according to the general method described in Example 5. The solution was deoxygenated with a helium sparge for 5 minutes and then was sealed under an argon atmosphere and heated overnight at 55° C. The solution was then diluted to a final volume of 200 ml with deionized water and 4.00 g (18.7 mmol) of sodium periodate were added. The oxidation was allowed to proceed overnight at room temperature. The product was dialyzed against deionized water using 12,000–14,000 MWCO tubing and then was lyophilized to give 13.45 g of a white solid. The presence of aldehyde in the polymer was confirmed by a broad singlet at 9.50 ($CDCl_3$) in the NMR spectrum.

Example 27

Copolymer of Acrylamide and N-(3-Aminopropyl) methacrylamide Hydrochloride using N-(2-Mercaptoethyl)-3,5-bis(4-benzoylbenzyloxy) benzamide A photoactivatable copolymer of the present invention was prepared in the following manner. Acrylamide, 3.671 g (51.6 mmol), was dissolved in 52.6 ml of DMSO, followed by the addition of 1.044 g (5.78 mmol) of N-(3-aminopropyl)methacrylamide hydrochloride, 0.246 g (1.50 mmol) of AIBN, and 0.303 g (0.50 mmol) of N-(2-mercaptoethyl)-3,5-bis(4-benzoylbenzyloxy)benzamide, prepared according to the general method described in Example 5. The solution was deoxygenated with a helium sparge for 5 minutes and then sealed under an argon atmosphere. The sealed vessel was then heated overnight at 55° C. to complete the polymerization. The polymer was precipitated by pouring into 550 ml of ether and the isolated solid was resuspended in 400 ml of chloroform before a final filtration. Vacuum drying gave 5.28 g of final product. Analysis of the amine content using the trinitrobenzenesulfonic acid method found 0.088 mmol/g of polymer, 76% of theoretical.

Example 28

Copolymer of Acrylamide and 2-Acrylamido-2-methylpropanesulfonic Acid using N-(2-Mercaptoethyl)-3,4,5-tris(4-benzoylbenzyloxy) benzamide A photoactivatable copolymer of the present invention was prepared in the following manner. Acrylamide, 0.785 g (11.0 mmol), was dissolved in 10.6 ml of DMSO, followed by the addition of 0.134 g (0.586 mmol) of 2-acrylamido-2-methylpropanesulfonic acid, 0.035 g (0.20 mmol) of AIBN, and 0.081 g (0.10 mmol) of N-(2-mercaptoethyl)-3,4,5-tris(4-benzoylbenzyloxy)-benzamide, prepared according to the general method described in Example 8. The solution was deoxygenated with a helium sparge for 10 minutes and then sealed under an argon atmosphere. The sealed vessel was then heated overnight at 55° C. to complete the polymerization. The polymer was precipitated by pouring the DMSO solution into 100 ml of ether. The solid was resuspended twice in 100 ml of chloroform to give 1.06 g of product after vacuum drying.

Example 29

Copolymer of Acrylamide and 2-Acrylamido-2-methylpropanesulfonic Acid using 1,4-Bis(4-benzoylbenzyloxy)-2-mercaptobutane A photoactivatable copolymer of the present invention was prepared in the following manner. Acrylamide, 1.094 g (15.4 mmol), was dissolved in 14.8 ml of DMSO, followed by the addition of 0.187 g (0.817 mmol) of 2-acrylainido-2-methylpropanesulfonic acid, 0.044 g (0.27 mmol) of AIBN, and an estimated 0.069 g (0.135 mmol) of 1,4-bis(4-benzoylbenzyloxy)-2-mercaptobutane, prepared according to the method described in Example 9. The solution was deoxygenated with a helium sparge for 10 minutes and then sealed under an argon atmosphere. The sealed vessel was then heated overnight at 55° C. to complete the polymerization. The polymer was precipitated by pouring the DMSO solution into 200 ml of acetone. The solid was resuspended three times in 100 ml of acetone to give 1.3 g of product after vacuum drying.

Example 30

Copolymer of Acrylamide and 2-Acrylamido-2-methylpropanesulfonic Acid using N-(2-Mercaptoethyl)-4-[4-(3,3,4,4,5,5,6,6,7,7,8,8,9,9,10,10,10-heptadecafluoro-2-thiadecyl)benzoyl] benzamide A photoactivatable copolymer of the present invention is prepared in the following manner. Acrylamide, 1.094 g (15.4 mmol), is dissolved in 14.8 ml of DMSO, followed by the addition of 0.187 g (0.817 mmol) of 2-acrylamido-2-methylpropanesulfonic acid, 0.044 g (0.27 mmol) of AIBN, and 0.101 g (0.135 mmol) of N-(2-mercaptoethyl)-4-[4-(3,3,4,4,5,5,6,6,7,7,8,8,9,9,10,10,10-heptadecafluoro-2-thiadecyl)benzoyl]benzamide, prepared according to the method described in Example 10. The solution is deoxygenated with a helium sparge for 10 minutes and then sealed under an argon atmosphere. The sealed vessel is heated overnight at 55° C. to complete the polymerization. The resulting polymer is precipitated by pouring the DMSO solution in excess ether. The resulting solid is then washed with chloroform and dried under vacuum.

Example 31

Improved Wettability of Polypropylene Using a Polyacrylamide Prepared with 4-Mercaptomethylbenzophenone A polyacrylamide prepared according to the general method described in Example 13 was dissolved in deionized water at 20 mg/ml. 1-Hexanol was added to make the solution 0.58% 1-hexanol in water to aid wetting of the fabric with the polymer solution. Melt blown polypropylene disks (1 inch diameter) were immersed in the polymer solution for two minutes, then removed and illuminated for two minutes on each side while still wet using a Dymax lighting system having a 400 watt medium pressure mercury bulb. The illumination distance was 250 cm (10 in.), giving an illumination intensity of approximately 2.0 mW/cm$^2$ at the 330–340 nm wavelength measured. Control disks were immersed in the polymer solution, but were not illuminated. The disks were then washed by placing them singly in membrane holders and passing 5×10 ml of deionized water through the fabric disks. The disks were dried by pressing between dry paper towels until no more water was removed, followed by air drying for at least 10 minutes. The fabric disks were tested for wettability by adding drops of water to the disks. Water added to the polymer coated disks was immediately absorbed into the fabric whereas water placed on control disks remained beaded on the surface.

Example 32

Reduction in Protein Binding Using a Polyacrylamide Prepared with N-(2-Mercaptoethyl)-4-benzoylbenzamide Polysulfone (10,000 nominal molecular weight cutoff) and polycarbonate (0.1 μm pores) membrane disks (19 mm diameter) were soaked overnight at room temperature on a shaker in a 10 mg/ml solution of the polymer prepared according to the general method of Example 14. The membranes were illuminated wet, one minute on each side, using a lighting system as described in Example 31. They were then washed in water for 2×30 minutes. They were blotted to remove excess water, but not completely dried. The membranes were placed into vials containing either bovine serum albumin (BSA)($^3$H-250 dpm/μg) or a horseradish peroxidase-streptavidin ("HRP-SA") conjugate at 1μg/ml. The vials were shaken overnight at 35° C. The membranes exposed to BSA were then washed and counted in a liquid scintillation counter. The membranes exposed to HRP-SA were washed and tested using a colorimetric assay for peroxidase activity. On polycarbonate membranes, the amounts of BSA absorbed was reduced 17% and the HRP-SA was reduced 19% compared with uncoated membranes. On polysulfone membranes, the BSA absorbed was reduced 54% and HRP-SA was reduced 39% compared with uncoated membranes.

Example 33

Protein A Immobilization Using a Copolymer of Acrylamide and N-Succinimidyl 6-Maleimidohexanoate Prepared with N-(2-Mercaptoethyl)-4-benzoylbenzamide The copolymer, prepared according to the general method described in Example 15, was dissolved at 10 mg/ml in 50% IPA/50% of 25 mM phosphate buffer, pH 7. The solution was applied to one inch disks of regenerated cellulose membranes (RC) with a pore size of 0.45 µm. After incubation for 2 minutes, the membranes were dried. The disks were illuminated for 1 minute on each side using the lighting system described in Example 31. The membranes were then washed with 25% IPA to remove unbound polymer and dried. Protein A solution (100 µl) at 5 mg/ml in PBS was applied to the reactive membranes and dried onto the membrane for 1–1.5 hours at room temperature. The Protein A membranes were then washed to remove unbound Protein A by passing solutions through the coated disks in membrane holders. The membranes were washed sequentially with: 1) 0.1 M glycine in 2% acetic acid, 2) 10× PBS, 3) PBS. The washed membranes were stored in 10× PBS at 4° C. The Protein A coated disks were evaluated by determination of the IgG binding capacity. Rabbit serum (2 ml) was diluted 1:5 in PBS and passed through the coated membranes at 1 ml/min. The disks were then washed with PBS to remove unbound protein. The bound IgG was eluted with 0.1 M glycine in 2% acetic acid. The amount of eluted IgG was determined by measuring the absorbance of the eluant at 280 nm and using an extinction coefficient of 1.4 ml/cm-mg. The IgG binding capacity was 103 and 80 $\mu g/cm^2$ respectively for each of 2 assay cycles.

Example 34

Protein A Immobilization Using an Oxidized Copolymer of N-Vinylpyrrolidone and 3-Allyloxy-1,2-propanediol Prepared with N-(2-Mercaptoethyl)-4-benzoylbenzamide The copolymer, prepared according to the general method described in Example 16, was coated onto membranes as described in Example 33 except that the polymer was applied at 5 and 2 mg/ml. Protein A was immobilized as described in Example 33, except that the protein A was coupled in pH 9 carbonate buffer and, after reacting the Protein A solution, 1 mg/ml of sodium borohydride in cold PBS was added to the disks and incubated for 15 minutes to reduce the Schiff base. The IgG binding capacities were 235 and 217 $\mu g/cm^2$ respectively for disks coated with 5 and 2 mg/ml polymer solutions as determined with the evaluation system described in Example 33.

Example 35

Oligonucleotide Immobilization Using a Maleimide Derivatized Copolymer of Acrylamide and N-(3-Aminopropyl)methacrylamide Hydrochloride Prepared with N-(2-Mercaptoethyl)-4-benzoylbenzamide The copolymer, prepared according to the general method described in Example 17, was diluted at 5 mg/ml in H$_2$O. The suspension was applied at 100 µl/well to E.I.A. medium binding flat bottom microplates (Corning Costar) and incubated for 2 hours. Excess reagent was removed and the plates were air dried in the dry room for 1 hour, followed by UV illumination for 2 minutes using the lighting system described in Example 31. The wells were then washed two times in H$_2$O. Uncoated and coated wells were incubated with 15 pmole/50 µl of a fluorescently labeled 33-mer oligonucleotide, modified with a sulfhydryl group on its 5'-end or with an identical oligonucleotide without the 5' thiol modification. Oligonucleotides were incubated for 2 hours at room temperature. The wells were then washed twice with 5X SSPE (0.9 M NaCl, 50 mM Na$_3$PO$_4$, pH 7.4, 5 mM EDTA) containing 0.5% SDS at 30° C. Oligonucleotide binding was evaluated using a fluorescence microscope. The results represent triplicate wells/experiment in two separate experiments.

No fluorescence was observed for either oligonucleotide in uncoated wells. Minimal fluorescence was observed in coated wells either containing no oligonucleotide or the unmodified oligonucleotide (+1, on a 1–4 scale). In contrast, fluorescence was markedly increased in the coated wells containing the thiol-modified oligonucleotide (+3).

Example 36

Improved Wettability of Polypropylene Using Polyvinylphosphonic Acid Prepared with N-(2-Mercaptoethyl)-4-benzoylbenzamide The polymer, prepared according to the general method described in Example 18, was dissolved at 10 mg/ml in deionized water containing 0.58% 1-hexanol (v/v). The coating process and evaluation were the same as described in Example 31. Water added to the polymer coated disks was immediately absorbed into the fabric whereas water placed on control disks remained beaded on the surface.

Example 37

Protein A Immobilization Using a Copolymer of Acrylamide and 2-Vinyl-4,4-dimethyl-2-oxazolin-5-one Prepared with N-(2-Mercaptoethyl)-4-benzoylbenzamide The polymer, prepared according to the general method described in Example 19, was coated onto membranes as described in Example 33 except that the polymer was applied at 5 mg/ml in water and the Protein A was coupled in pH 9 carbonate buffer. The IgG capacity was 117 $\mu g/cm^2$ as determined with the evaluation system described in Example 33.

Example 38

Protein A Immobilization Using a Copolymer of Acrolein and N-Vinylpyrrolidone Prepared with N-(2-Mercaptoethyl-4-benzoylbenzamide The copolymer, prepared according to the general method described in Example 20, was coated onto polysulfone membranes (Gelman HT-450, 0.45 µm pore size) as described in Example 33 except that the polymer was applied at 1 mg/ml. Protein A was immobilized as described in Example 33, except that the protein A was coupled in pH 9 carbonate buffer and, after reacting the Protein A solution, 1 mg/ml of sodium borohydride in cold PBS was added to the disks and incubated for 15 minutes to reduce the Schiff base. The IgG binding capacity was 22 $\mu g/cm^2$ as determined with the evaluation system described in Example 33.

Example 39

Reduction in Protein Binding Using a Polyacrylamide Prepared with N-(2-Mercaptoethyl)-2,6-bis(4-benzoylbenzamido)hexanamide The polyacrylamide, prepared in a method analogous to Example 21 without prior purification of the chain transfer agent, was dissolved in deionized water at 1.0 mg/ml. The polymer solution was added to polystyrene microplate wells (200 μl per well) and incubated overnight at room temperature. After incubation, 150 μl were removed from each well and the plate was placed in a plastic bag and illuminated for two minutes using the lighting system described in Example 31. After illumination, it was washed ten times with deionized water. To each well was added 100 μl of a HRP-SA conjugate followed by incubation for six hours. The plates were then washed ten times with deionized water followed by color generation using hydrogen peroxide and tetramethylbenzidine and the color measured at 655 nm in a microplate reader. The average absorbance reading (five replicates) for the polymer-coated wells was 0.179 compared with 1.057 for uncoated wells.

Example 40

Reduction in Protein Binding Using a Polyacrylamide Prepared with N,N-Bis[2-(4-benzoylbenzyloxy)ethyl]-4-mercaptobutanamide The polyacrylamide, prepared according to the general method described in Example 22, was dissolved in deionized water at 5 mg/ml and 200 μl were applied per well of polystyrene microplates. The polymer solution was left in the wells overnight, then removed and the plates illuminated two minutes in a plastic bag to keep them from drying. The lighting system described in Example 31 was used for the illumination. The plates were then washed five times with deionized water after which 100 μl of a HRP-SA conjugate solution in phosphate buffered saline were added and incubated for seven hours at room temperature. After thorough washing with deionized water, color was generated from the adsorbed peroxidase using tetramethylbenzidine and measured in a microplate reader at 655 nm. Polymer-coated wells had an average absorbance reading of 0.333 compared with uncoated wells with an average absorbance of 2.45.

Example 41

Reduction in Protein Binding Using a Polyacrylamide Prepared with N-(2-Mercaptoethyl)-3,5-bis(4-benzoylbenzyloxy)benzamide The polyacrylamide, prepared according to the general method described in Example 23, was coated onto PS microplates and tested as in Example 40. Polymer-coated wells had an average absorbance reading of 0.122 compared with uncoated wells with an average absorbance of 2.45.

Example 42

Reduction in Protein Binding Using a Polyvinylpyrrolidone Prepared with N-(2-Mercaptoethyl)-3,5-bis(4-benzoylbenzyloxy)benzamide The polyvinylpyrrolidone, prepared according to the general method described in Example 24, was dissolved at 5 mg/ml in deionized water. The turbid solution was filtered through porous polypropylene disks to remove any particulates. To wells of polystyrene microplates were added 150 μl of the polymer solution. After incubating overnight at room temperature, the plates were illuminated for one minute using the lighting system described in Example 31. The plates were washed five times with water. Radiolabelled protein solutions (100 μl per well) were added to coated and uncoated wells and incubated overnight at room temperature. The protein solutions used were bovine serum albumin (BSA) at 0.1 mg/ml, immunoglobulin G (IgG) at 0.02 mg/ml and ribonuclease (RNase) at 0.1 mg/ml. After incubation with the protein solutions, the wells were washed five times with phosphate buffered saline. The wells were separated from the plate strips and dissolved in tetrahydrofuran and counted in a liquid scintillation counter. Compared with uncoated controls, the polymer-coated wells had the following reductions in protein adsorbed: BSA—83%, IgG—92% and RNase—89%.

Example 43

Protein A Immobilization Using a Copolymer of Acrylamide and N-Succinimidyl 6-Maleimidohexanoate Prepared with N-(2-Mercaptoethyl)-3,5-bis(4-benzoylbenzyloxy)benzamide The copolymer, prepared according to the general method described in Example 25, was coated onto membranes as described in Example 33 except that the polymer was applied at 5 and 2 mg/ml in 50% IPA and the disks were incubated for 5 minutes and dried and the Protein A was coupled in PBS. The IgG capacity was 185 and 163 $\mu g/cm^2$ respectively for each of two assay cycles as determined with the evaluation system described in Example 33.

Example 44

Protein A Immobilization Using an Oxidized Copolymer of N-Vinylpyrrolidone and 3-Allyloxy-1,2-propanediol Prepared with N-(2-Mercaptoethyl)-3,5-bis(4-benzoylbenzyloxy)benzamide The copolymer, prepared according to the general method described in Example 26, was coated onto RC membranes as described in Example 33 except that the polymer was applied at 5 and 1 mg/ml. Protein A was immobilized as described in Example 33, except that the protein A was coupled in pH 9 carbonate buffer and, after reacting the Protein A solution, 1 mg/ml of sodium borohydride in cold PBS was added to the disks and incubated for 15 minutes to reduce the Schiff base. The IgG binding capacities were 121 and 70 $\mu g/cm^2$ respectively for disks coated with 5 and 1 mg/ml polymer solutions as determined with the evaluation system described in Example 33.

Example 45

Improved Wettability of Polypropylene Using a Copolymer of Acrylamide and N-(3-Aminopropyl)methacrylamide Hydrochloride Prepared with N-(2-Mercaptoethyl)-3,5-bis(4-benzoylbenzyloxy)benzamide The copolymer, prepared according to the general method described in Example 27, was dissolved at 10 mg/ml in deionized water containing 0.58% 1-hexanol (v/v). The coating process and evaluation were the same as described in Example 31. Water added to the polymer coated disks was immediately absorbed into the fabric whereas water placed on control disks remained beaded on the surface.

Example 46

Improved Wettability of Polypropylene Using a Copolymer of Acrylamide and 2-Acrylamido-2-methylpropanesulfonic Acid Prepared with N-(2-Mercaptoethyl)-3,4,5-tris(4-benzoylbenzyloxy) benzamide The copolymer, prepared according to the general method described in Example 28, was dissolved at 10 mg/ml in deionized water containing 0.58% 1-hexanol (v/v). The coating process and evaluation were the same as described in Example 31. Water added to the polymer coated disks was immediately absorbed into the fabric whereas water placed on control disks remained beaded on the surface.

Example 47

Improved Wettability of Polypropylene Using a Copolymer of Acrylamide and 2-Acrylamido-2-methylpropanesulfonic Acid Prepared with 1.4-Bis (4-benzoylbenzyloxy)-2-mercaptobutane The copolymer, prepared according to the general method described in Example 29, was dissolved at 10 mg/ml in deionized water containing 0.58% 1-hexanol. The coating process and evaluation were the same as described in Example 31. Water added to the polymer coated disks was immediately absorbed into the fabric whereas water placed on control disks remained beaded on the surface.

We claim:

1. An agent useful as a chain transfer agent, in combination with a different free radical generator, to prepare a semitelechelic polymer having an end group comprising one or more photoactivatable groups, the agent being selected from the group consisting of:

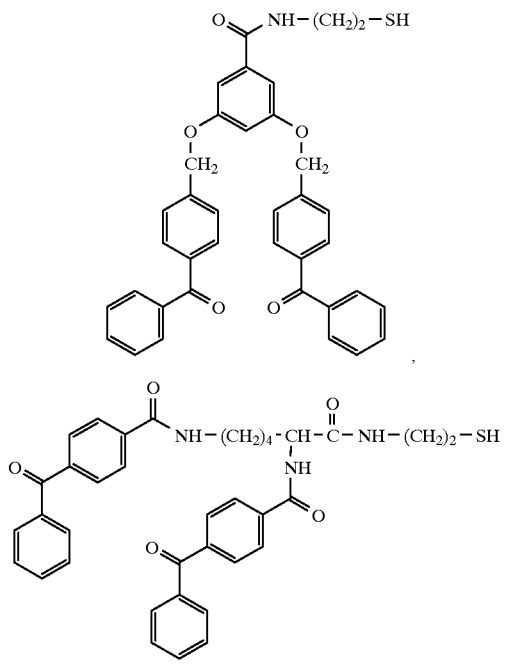

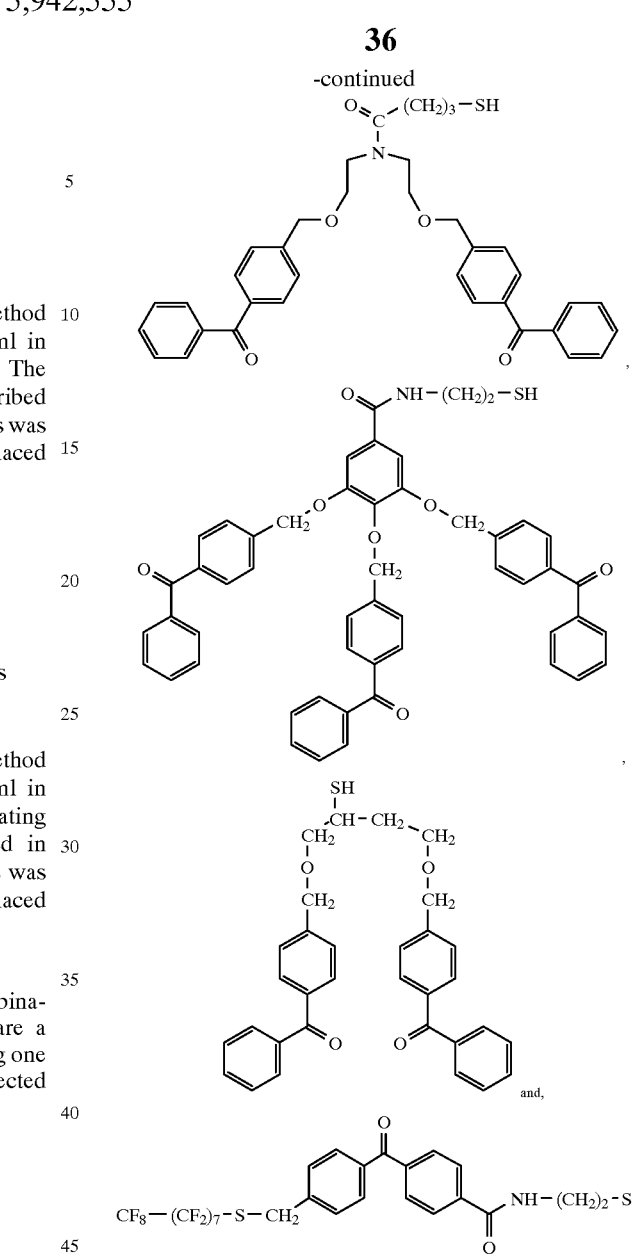

2. A method of preparing a semitelechelic polymer, the method comprises the steps of;
    a) providing a chain transfer agent having one or more photoactivatable aryl ketone group(s) and one or more sulfhydryl group(s),
    b) providing one or more suitable monomers, and
    c) thermally initiating the free radical polymerization of the monomers, by the use of the chain transfer agent and a different free radical generator, to provide at least one semitelechelic polymer chain having an end group comprising the one or more photoactivatable aryl ketone groups,
wherein each chain transfer group is capable of serving as an initiation site for the growth of a new polymer chain.

3. A method according to claim 2 wherein the photoactivatable groups and sulfhydryl groups are attached by means of a spacer radical.

4. A method according to claim 3 wherein the spacer radical is selected from the group consisting of substituted or unsubstituted alkylene, oxyalkylene, cycloalkylene, arylene, oxyarylene, or aralkylene groups.

5. A method according to claim 3 wherein the aryl ketones are selected from the group consisting of acetophenone, benzophenone, anthraquinone, anthrone, and heterocyclic analogues of anthrone.

6. A method according to claim 2 wherein the chain transfer agent is selected from the agent of claim 1.

7. A method according to claim 2 wherein the chain transfer agent is selected from the group consisting of:

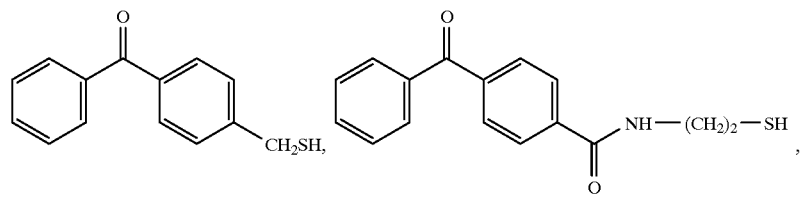

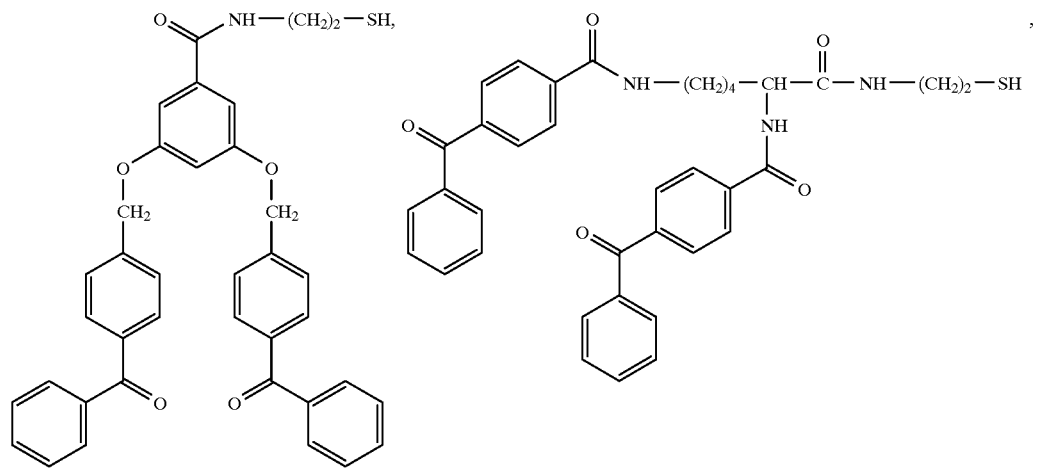

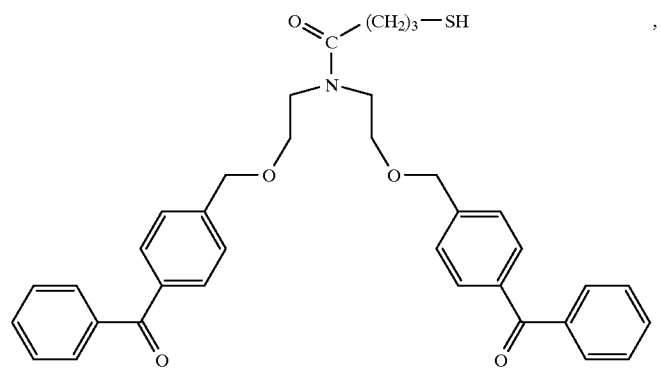

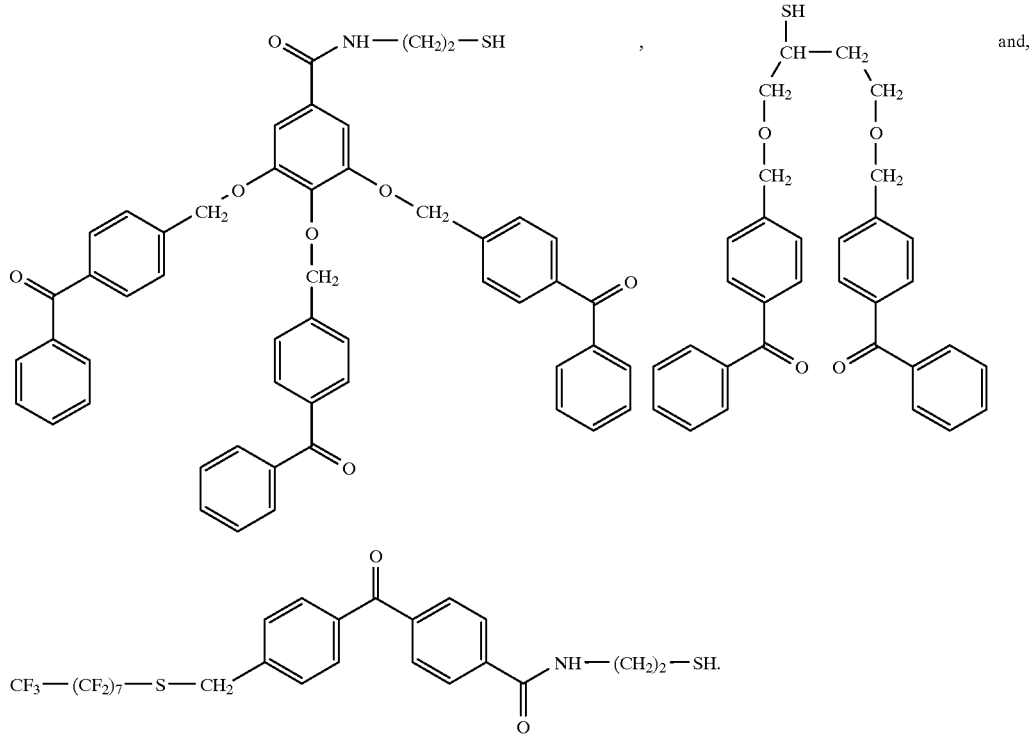

8. A support surface bearing synthetic polymers prepared according to the method of claim 2.

9. A surface according to claim 8 wherein the chain transfer agent comprises a single chain transfer group.

10. A surface according to claim 8 wherein the photoactivatable groups and chain transfer groups are attached by means of a spacer radical.

11. A surface according to claim 10 wherein the spacer radical is selected from the group consisting of substituted or unsubstituted alkylene, oxyalkylene, cycloalkylene, arylene, oxyarylene, or aralkylene groups.

12. A surface according to claim 10 wherein the aryl ketones are selected from the group consisting of acetophenone, benzophenone, anthraquinone, anthrone, and heterocyclic analogues of anthrone.

13. A support surface according to claim 8 wherein the chain transfer agent is selected from the agents of claim 1.

14. A synthetic polymer comprising polymerized monomer units and at least one end group comprising one or more photoactivatable groups wherein the polymer is prepared by a method that comprises the steps of:
   a) providing a chain transfer agent having one or more photoactivatable aryl ketone group(s) and one or more sulfhydryl group(s),
   b) providing one or more suitable monomers, and
   c) thermally initiating the free radical polymerization of the monomers, by the use of the chain transfer agent and a different free radical generator, to provide at least one semitelechelic polymer chain having an end group comprising the one or more photoactivatable aryl ketone groups, wherein each chain transfer group is capable of serving as an initiation site for the growth of a new polymer chain.

15. A synthetic polymer according to claim 14 wherein the aryl ketones are each selected from the group consisting of acetophenone, benzophenone, anthraquinone, anthrone, and heterocyclic analogues of anthrone, and the chain transfer groups comprise sulfhydryl compounds.

16. A polymer according to claim 14 wherein the chain transfer agent comprises a single sulfhydryl group.

17. A polymer according to claim 14 wherein the photoactivatable groups and chain transfer groups are attached by means of a spacer radical.

18. A polymer according to claim 17 wherein the spacer radical is selected from the group consisting of substituted or unsubstituted alkylene, oxyalkylene, cycloalkylene, arylene, oxyarylene, or aralkylene groups.

19. A polymer according to claim 17 wherein the aryl ketones are selected from the group consisting of acetophenone, benzophenone, anthraquinone, anthrone, and heterocyclic analogues of anthrone.

20. A synthetic polymer according to claim 14 wherein the chain transfer agent is selected from the agents of claim 1.

21. A synthetic polymer according to claim 14 wherein the chain transfer agent is selected from the group consisting of:

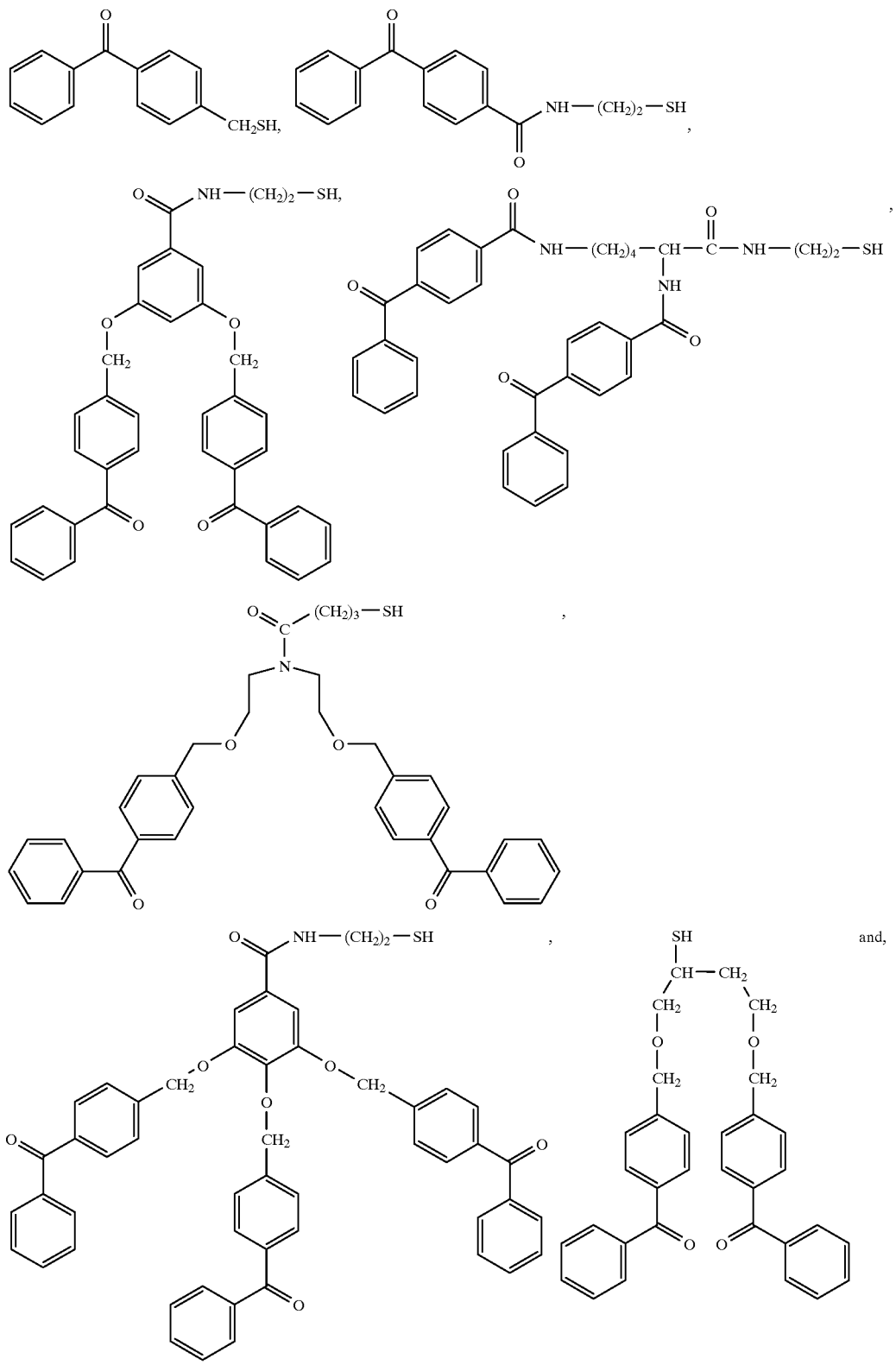

-continued

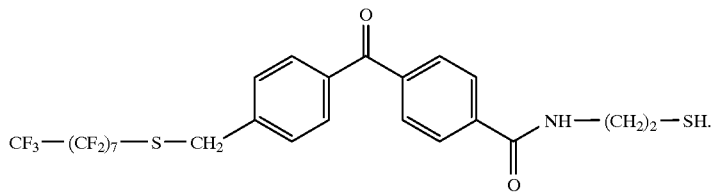

22. A method of treating a support surface, the method comprising the steps of providing a polymer according to claim 14, contacting the polymer with the support surface under conditions in which the photoactivatable group can orient itself to the surface, and activating the oriented photoactivatable group in order to covalently attach the polymer to the surface.

23. A method according to claim 22 wherein the chain transfer agent comprises a single chain transfer group.

24. A method according to claim 22 wherein the photo-activatable groups and chain transfer groups are attached by means of a spacer radical.

25. A method according to claim 24 wherein the spacer radical is selected from the group consisting of substituted or unsubstituted alkylene, oxyalkylene, cycloalkylene, arylene, oxyarylene, or aralkylene groups.

26. A method according to claim 24 wherein the aryl ketones are selected from the group consisting of acetophenone, benzophenone, anthraquinone, anthrone, and heterocyclic analogues of anthrone.

27. A method according to claim 22 wherein the chain transfer agent is selected from the agents of claim 1.

* * * * *

UNITED STATES PATENT AND TRADEMARK OFFICE
CERTIFICATE OF CORRECTION

PATENT NO. : 5,942,555
DATED : August 24, 1999
INVENTOR(S) : Swanson, et al.

It is certified that error appears in the above-identified patent and that said Letters Patent is hereby corrected as shown below:

Column 8, line 1, replace "—($CH_2$=$CHR_4R_5$)—" with -- —($CH_2$—$CHR_4$)— --.

Signed and Sealed this

Twelfth Day of December, 2000

Attest:

Attesting Officer

Q. TODD DICKINSON
Director of Patents and Trademarks

UNITED STATES PATENT AND TRADEMARK OFFICE
CERTIFICATE OF CORRECTION

PATENT NO. : 5,942,555 Page 1 of 1
APPLICATION NO. : 08/619303
DATED : August 24, 1999
INVENTOR(S) : Swanson et al.

It is certified that error appears in the above-identified patent and that said Letters Patent is hereby corrected as shown below:

Column 7, line 23, replace "sulfhlydryl" with --sulfhydryl--.

Column 21, line 66, replace "fmal" with --final--.

Column 26, line 42, replace "ThF" with --THF--.

Column 27, line 67, replace "N-vinylpyffolidone" with --N-Vinylpyrrolidone--.

Column 29, line 47, replace "2-acrylaindo-" with --2-acrylamido- --.

Column 32, line 6, replace "H2 O" with --H2O--.

Claim 1, line 44 in the chemical structure, replace "CF8" with --CF3--.

Signed and Sealed this

Twentieth Day of February, 2007

JON W. DUDAS
*Director of the United States Patent and Trademark Office*